United States Patent
Irvine et al.

(10) Patent No.: US 12,139,721 B2
(45) Date of Patent: Nov. 12, 2024

(54) CONTROL OF REPLICATION AND TRANSCRIPTION OF SELF-REPLICATING RNA IN RESPONSE TO SMALL MOLECULES

(71) Applicant: Massachusetts Institute of Technology, Cambridge, MA (US)

(72) Inventors: Darrell J. Irvine, Arlington, MA (US); Ron Weiss, Newton, MA (US); Yingzhong Li, Quincy, MA (US); Jan Lonzaric, Arlington, MA (US); Parisa Yousefpour, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 110 days.

(21) Appl. No.: 17/231,588

(22) Filed: Apr. 15, 2021

(65) Prior Publication Data
US 2021/0324413 A1    Oct. 21, 2021

Related U.S. Application Data

(60) Provisional application No. 63/011,047, filed on Apr. 16, 2020.

(51) Int. Cl.
*C12N 15/86* (2006.01)
*A61K 31/505* (2006.01)
*A61K 31/713* (2006.01)

(52) U.S. Cl.
CPC ............ *C12N 15/86* (2013.01); *A61K 31/505* (2013.01); *A61K 31/713* (2013.01);
(Continued)

(58) Field of Classification Search
CPC .......... C12N 15/86; C12N 2720/12322; C12N 2720/12343; C12N 2820/60;
(Continued)

(56) References Cited

U.S. PATENT DOCUMENTS 11,351,271 B2 *  6/2022  Weiss .................... C12N 15/85
2018/0296702 A1 * 10/2018  Weiss et al.
(Continued)

FOREIGN PATENT DOCUMENTS

WO    WO 2019/152406 A1    8/2019

OTHER PUBLICATIONS

Jin et al. 2019 (Building an Inducible T7 RNA Polymerase/T7 Promoter Circuit in *Synechocystis* sp. PCC6803. ACS Synth. Biol. 8: 655-660) (Year: 2019).*

(Continued)

*Primary Examiner* — Kimberly Chong
*Assistant Examiner* — Ruth Sophia Arieti
(74) *Attorney, Agent, or Firm* — Wolf, Greenfield & Sacks, P.C.

(57) ABSTRACT

Genetic circuits have been developed to regulate behaviors of replicon RNA in responses to small molecules, which has broader applications, such as for quantitative expression of cargo genes, temporary expression of immunomodulatory cytokines or antigens for better cancer immunotherapy or vaccination, and for increased safety in use of self-replicating vectors or in combination with other viral-delivery vectors. Described herein are genetic circuits suitable for systems that either require a tight off state or a slow off state, which can serve for instance where either a kill switch or prolonged protein expression (e.g., of vaccine antigens) are needed.

20 Claims, 6 Drawing Sheets
Specification includes a Sequence Listing.

(52) U.S. Cl.
CPC .............. *C12N 2720/12322* (2013.01); *C12N 2720/12343* (2013.01); *C12N 2820/60* (2013.01)

(58) Field of Classification Search
CPC ........... C12N 2770/36122; C12N 2770/36143; A61K 31/505; A61K 31/713; C07K 2319/00; C07K 14/005
See application file for complete search history.

(56) References Cited

U.S. PATENT DOCUMENTS

| | | | |
|---|---|---|---|
| 2019/0151474 A2 | 5/2019 | Weiss et al. | |
| 2020/0071723 A1* | 3/2020 | Gao | C07K 14/005 |
| 2020/0283796 A1 | 9/2020 | Weiss et al. | |

OTHER PUBLICATIONS

Datta et al. 2018. A Destabilizing Domain Allows for Fast, Noninvasive, Conditional Control of Protein Abundance in the Mouse Eye—Implications for Ocular Gene Therapy. IVOS 59[12]:4909-4920 (Year: 2018).*
Rupp et al. 2015. Alphavirus RNA synthesis and nonstructural protein functions. J. Gen. Virol 96:2483-2500 (IDS Doc) (Year: 2015).*
U.S. Appl. No. 17/320,965, filed Jul. 2021.*
U.S. Appl. No. 18/310,039, filed May 2023.*
Banaszynski et al., A rapid, reversible, and tunable method to regulate protein function in living cells using synthetic small molecules. Cell. Sep. 8, 2006;126(5):995-1004.
Bogers et al., Potent immune responses in rhesus macaques induced by nonviral delivery of a self-amplifying RNA vaccine expressing HIV type 1 envelope with a cationic nanoemulsion. J Infect Dis. Mar. 15, 2015;211(6):947-55. doi: 10.1093/infdis/jiu522. Epub Sep. 18, 2014.
Ganesan et al., Synthetic RNA-protein modules integrated with native translation mechanisms to control gene expression in malaria parasites. Nat Commun. Mar. 1, 2016;7:10727.
Granot et al., Sindbis viral vectors transiently deliver tumor-associated antigens to lymph nodes and elicit diversified antitumor CD8+ T-cell immunity. Mol Ther. Jan. 2014;22(1):112-22. doi: 10.1038/mt.2013.215. Epub Sep. 12, 2013.
Grimley et al, Synthesis and analysis of stabilizing ligands for FKBP-derived destabilizing domains. Bioorg Med Chem Lett. Jan. 15, 2008;18(2):759-61. doi: 10.1016/j.bmcl.2007.11.044. Epub Nov. 17, 2007.
Iwamoto et al., A general chemical method to regulate protein stability in the mammalian central nervous system. Chem Biol. Sep. 24, 2010;17(9):981-8.
Li et al., In vitro evolution of enhanced RNA replicons for immunotherapy. Sci Rep. May 6, 2019;9(1):6932. doi: 10.1038/s41598-019-43422-0. PMID: 31061426; PMCID: PMC6502795.
Lundstrom, Self-replicating RNA viruses for RNA therapeutics. Molecules. 2018; 23(12):3310.
Lundstrom, Replicon RNA Viral Vectors as Vaccines. Vaccines (Basel). Nov. 7, 2016;4(4):39.
Maximov et al., Endoxifen, 4-Hydroxytamoxifen and an Estrogenic Derivative Modulate Estrogen Receptor Complex Mediated Apoptosis in Breast Cancer. Mol Pharmacol. Aug. 2018;94(2):812-822. doi: 10.1124/mol.117.111385. Epub May 8, 2018.
Miyazaki et al., Destabilizing domains derived from the human estrogen receptor. J Am Chem Soc. Mar. 7, 2012;134(9):3942-5. doi: 10.1021/ja209933r. Epub Feb. 22, 2012.
Osada et al., Novel recombinant alphaviral and adenoviral vectors for cancer immunotherapy. Semin Oncol. Jun. 2012;39(3):305-10.
Petrakova et al., Noncytopathic replication of Venezuelan equine encephalitis virus and eastern equine encephalitis virus replicons in Mammalian cells. J Virol. Jun. 2005;79(12):7597-608. doi: 10.1128/JVI.79.12.7597-7608.2005.
Rupp et al., Alphavirus RNA synthesis and non-structural protein functions. J Gen Virol. Sep. 2015;96(9):2483-2500. doi: 10.1099/jgv.0.000249. Epub Jul. 24, 2015.
Shin et al., Structural and functional insights into alphavirus polyprotein processing and pathogenesis. Proc Natl Acad Sci U S A. Oct. 9, 2012;109(41):16534-9. doi: 10.1073/pnas.1210418109. Epub Sep. 25, 2012. PMID: 23010928; PMCID: PMC3478664.
Vogel et al., Self-Amplifying RNA Vaccines Give Equivalent Protection against Influenza to mRNA Vaccines but at Much Lower Doses. Mol Ther. Feb. 7, 2018;26(2):446-455. doi: 10.1016/j.ymthe.2017.11.017. Epub Dec. 5, 2017.
Wroblewska et al., Mammalian synthetic circuits with RNA binding proteins for RNA-only delivery. Nat Biotechnol. Aug. 2015;33(8):839-41. doi: 10.1038/nbt.3301. Epub Aug. 3, 2015.
Andries et al., Synthetic biology devices and circuits for RNA-based 'smart vaccines': a propositional review. Expert Rev Vaccines. Feb. 2015;14(2):313-31.
Ljungberg et al., Self-replicating alphavirus RNA vaccines. Expert Rev Vaccines. Feb. 2015;14(2):177-94. doi: 10.1586/14760584.2015.965690. Epub Oct. 1, 2014.
Pietila et al., Alphavirus polymerase and RNA replication. Virus Res. Apr. 15, 2017;234:44-57. doi: 10.1016/j.virusres.2017.01.007. Epub Jan. 16, 2017.
Wagner et al., Small-molecule-based regulation of RNA-delivered circuits in mammalian cells. Nat Chem Biol. Nov. 2018;14(11):1043-1050. doi: 10.1038/s41589-018-0146-9. Epub Oct. 16, 2018.
Zappasodi et al., Alphavirus-based vaccines in melanoma: rationale and potential improvements in immunotherapeutic combinations. Immunotherapy. 2015;7(9):981-97. doi: 10.2217/imt.15.64. Epub Aug. 27, 2015.

* cited by examiner

CONTROL OF REPLICATION AND TRANSCRIPTION OF SELF-REPLICATING RNA IN RESPONSE TO SMALL MOLECULES

RELATED APPLICATION

This application claims the benefit under 35 U.S.C. § 119(e) of U.S. Provisional Application No. 63/011,047, entitled "CONTROL REPLICATION AND TRANSCRIPTION OF SELF-REPLICATING RNA IN RESPONSES TO SMALL MOLECULE TMP," filed on Apr. 16, 2020, the entire contents of which are incorporated herein by reference.

FEDERALLY SPONSORED RESEARCH

This invention was made with Government support under Grant No. R01 CA206218 and R01 EB025854 awarded by the National Institutes of Health (NIH). The Government has certain rights in the invention.

REFERENCE TO THE SEQUENCE LISTING

The present application is being filed along with a Sequence Listing in electronic format. The Sequence Listing is provided as a file entitled M065670511US01-SEQ-JRV.txt created on Apr. 15, 2021, which is 48,485 bytes in size. The information in electronic format of the sequence listing is incorporated herein by reference in its entirety.

FIELD OF THE INVENTION

The present application relates to genetic circuits suitable for the expression of output genes.

BACKGROUND

Genetic circuits are partially or fully synthetic genetic assemblages that are designed to perform specific functions, generally through the controlled expression of one or more encoded genes. The ability to accurately control the expression of genes comprised by a genetic circuit is important, especially for circuits intended for use in a human subject.

SUMMARY

The present disclosure provides various genetic circuits that may be controlled by small molecules. In one example, genetic circuits comprising DDd-nsP2 are suitable for systems that require a tight off state and could serve as a kill switch upon removal of TMP. On the other hand, genetic circuits comprising nsP3-DDd are suitable as an on-switch or slow off-switch in situations where leaky expression can be tolerated and/or where the level of the circuit's output must be maintained over a longer period to be efficacious, for example in the expression of antigens for a vaccine application.

According to one aspect, a genetic circuit for regulating responses of replicon RNA to small molecules is provided. Such a genetic circuit comprises a nsP2 and/or a nsP3, wherein the nsP2 is modified by fusion to a first DD and/or the nsP3 is modified by fusion to a second DD. In some embodiments the first DD is fused to the N-terminus of the modified nsP2. In some embodiments the second DD is fused to the C-terminus of the modified nsP3.

In some embodiments, the first DD and the second DD are selected from an E. coli DHFR-derived DD, a human estrogen receptor ligand binding domain-derived DD, and a FKBP-derived DD, wherein the first and second DDs may be of the same or different type. In some embodiments the DDs are stabilized in the presence of a small molecule selected from TMP, 4-OHT, and a Shield ligand. In some embodiments the first and second DDs are stabilized by the same or different small molecule.

In some embodiments, the genetic circuit further comprises a nsP1 and nsP4, which may be modified by fusion to a third and fourth DD, respectively. The third and fourth DD are selected from an E. coli DHFR-derived DD, a human estrogen receptor ligand binding domain-derived DD, and a FKBP-derived DD. The third and fourth DDs may be of the same or different type of DD and may each be of the same or different type of DD as either of the first and second DDs. In some embodiments the third and fourth DDs are stabilized in the presence of a small molecule selected from TMP, 4-OHT, and a Shield ligand. In some embodiments the third and fourth DDs are stabilized by the same or different small molecule, and may each be stabilized by the same or different small molecule as either of the first and second DDs.

In some embodiments, the modified nsP2 and modified nsP3 are encoded on one or more RNA replicons. In some embodiments, the one or more replicons may also encode nsP1 and nsP4. The RNA replicons may be one or more alphavirus-derived replicons, such as Venezuelan equine encephalitis (VEE) virus-derived replicons or Sindbis virus-derived replicons. In some embodiments, the replicons are replicated by an RdRp comprising nsP1, nsP2, nsP3, and nsP4.

In some embodiments, the replicons further comprise one or more nucleic acid molecules encoding one or more output sequences, wherein the one or more nucleic acid molecules are operably linked to one or more promoters, and replication of the one or more replicons by RdRp also replicates the one or more output sequences. The output sequences may be encoded on one or more replicons. The promoters may be constitutive or inducible. One or more of the output sequences may be operably linked to a subgenomic promoter. In some embodiments, each output sequence is a protein, a DNA, a RNA, or a miRNA. In some embodiments, the output sequence is a protein which is an antigen that stimulates an immune response.

In some embodiments, the expression of one or more output sequences from the genetic circuit is repressed by the expression of one or more effector sequences, wherein each effector sequence encodes a small molecule-regulatable RNA binding protein and is operably linked to a promoter. The small molecule-regulatable RNA binding protein may comprise a RNA binding protein that is fused to a small molecule-interacting domain. In some embodiments, the RNA binding protein is L7AE or DDX6. In some embodiments, the small molecule-interacting domain is a fifth DD selected from an E. coli DHFR-derived DD, a human estrogen receptor ligand binding domain-derived DD, and a FKBP-derived DD, which may be the same or different type of DD as any of the first, second, third, or fourth DDs. In some embodiments the small molecule-regulatable RNA binding protein is TetR. In some embodiments, expression of the one or more output sequences is derepressed in the presence of a small molecule selected from trimethoprim (TMP), 4-hydroxytamoxifen (4-OHT), Shield ligand, or doxycycline. Expression of the one or more effector sequences may be constitutive or inducible. The one or more effector sequences may be encoded on the one or more RNA replicons. One or more of the effector sequences may be operably linked to a subgenomic promotor.

According to another aspect, a cell is provided which comprises any of the above genetic circuits.

In some embodiments, the cell is a mammalian cell. In some embodiments the cell is a human induced pluripotent stem cell, a diseased cell, an immune cell, or a recombinant protein producing cell. In some embodiments, the genetic circuit is integrated into the genome of the cell.

According to another aspect, a non-human animal is provided which comprises any of the above genetic circuits or any of the above cells.

In some embodiments, the non-human animal is a mammal.

According to another aspect, a pharmaceutical composition is provided which comprises any of the above genetic circuits or any of the above cells, and a pharmaceutically acceptable carrier.

According to another aspect, a method is provided for expressing one or more output sequences in a subject. The method includes steps for administering to the subject an effective amount of one of the above genetic circuits which comprise one or more output sequences, and then controlling expression of one or more output sequences by administering a first and/or second small molecule to the subject. The genetic circuit comprises a nsP2 modified by fusion with a first DD and/or a nsP3 modified by fusion with a second DD, which are stabilized in the presence of the first or second small molecules, respectively.

In some embodiments, the genetic circuit further comprises a nsP1 modified by fusion with a third DD and/or a nsP4 modified by fusion with a fourth DD, which are stabilized in the presence of a third or fourth small molecule, respectively. In some embodiments any of the first, second, third, and fourth DD are selected from TMP, 4-OHT, or a Shield ligand.

In some embodiments, the method further includes a step of controlling expression of one or more output sequences by administering a fifth small molecule to the subject, wherein expression of one or more output sequences is derepressed in the presence of the fifth small molecule. The fifth small molecule derepresses expression of one or more output sequences by interacting with a small molecule-regulatable RNA-binding protein encoded by one or more effector sequences. The small molecule-regulatable RNA-binding protein may comprise a small molecule-interacting domain that is a fifth DD, which may be selected from an *E. coli* DHFR-derived DD, a human estrogen receptor ligand binding domain-derived DD, and a FKBP-derived DD. The small molecule-regulatable RNA-binding protein may comprise a small molecule-interacting domain that is TetR. The small molecule-regulatable RNA-binding protein may be stabilized in the presence of TMP, 4-OHT, Shield ligand, or doxycycline.

In some embodiments, each output sequence is a protein, DNA, RNA, or miRNA. In some embodiments, one or more output sequence is an antigen for stimulating an immune response. In some embodiments, the subject is a human.

The following Detailed Description references the accompanying drawings which form a part this application, and which show, by way of illustration, specific example implementations. Other implementations may be made without departing from the scope of the disclosure.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 3A: Illustration of tagging nsP2 with destabilization domain (DDd). FIG. 3B: Dose-dependence curve of intensity of cargo gene expressions (GFP; Y-axis) versus TMP concentration (X-axis). FIG. 3C: Quick turn-on and turn-off of mCherry expression in response to TMP. BHK21 cells were transfected with constitutive replicon RNA (C9-mCherry) or regulated replicon RNA (C9-DDd-nsP2-mCherry) in presence or absence of 1 µM TMP. At day 1, TMP was removed or added as indicated. Shown are mean fluorescence intensity (MFI) of mCherry at day 1 and 3 as indicated, as determined by flow cytometry.

FIG. 4A: Illustration of tagging nsP3 with destabilization domain (DDd). FIG. 4B: Dose-dependence curve of intensity of cargo gene expressions (GFP; Y-axis) versus TMP concentration (X-axis). FIGS. 4C-4D: Quick turn-on and slow turn-off of mCherry (FIG. 4C) and Luciferase (FIG. 4D) expression in response to TMP. BHK21 cells were transfected with constitutive replicon RNA (C9-mCherry, C9-Luciferase) or regulated replicon RNA (C9-nsP3-DDd-mCherry, C9-nsP3-DDd-Luciferase) in presence or absence of 1 µM TMP. At day 1, TMP was added as indicated (+). Shown are mean fluorescence intensity (MFI) of mCherry (FIG. 4C) or relevant luminescence unit (RLU) of luciferase (FIG. 4D) at day 1, 3, and 7 as indicated, determined by flow cytometry or by plate reader, respectively.

FIG. 5A: Luminescence intensity at 7 days post i.m. injection (n=8-12). From left to right, the following conditions are indicated: constitutive FLuc−TMP; constitutive FLuc+TMP; DD-FLuc−TMP (OFF); DD-FLuc+TMP (ON); nsP3-DD, FLuc−TMP (OFF); nsP3-DD, FLuc+TMP (ON); DD-nsP2, FLuc−TMP (OFF); DD-nsP2, FLuc+TMP (ON); nsP3-DD, DD-FLuc−TMP (OFF); nsP3-DD, DD-FLuc+TMP (ON). FIG. 5B: Time course of luminescence intensity in mice injected with replicons encoding DD-FLuc and encapsulated in lipid nanoparticles (LNPs). Dashed lines indicate presence of TMP and solid lines indicate no TMP (n=6). The dotted line shows the background levels of luminescence detected in untreated animals. Arrow indicates TMP switching. Data are from independent experiments. Where indicated, TMP was provided in diet. From top to bottom at 9 days post injection, the following conditions are indicated: ++TMP (ON); −+TMP (OFF-ON); +−TMP (ON-OFF); −−TMP (OFF).

FIG. 7A: Schematic illustration of an exemplary nsP3-DD gene circuit encoding IL12-MSA and gsdmD-DD. FIGS. 7B-7C: In vitro testing of gene expression from different replicon gene circuit designs in KP tumor cells. Replicons were transfected into the KP cells by electroporation and cell viability (FIG. 7B) and extracellular IL12 levels (FIG. 7C) were measured by flow cytometry and ELISA, respectively. For TMP treatment, it was added to the growth medium at 10 μM following electroporation. From left to right, the following conditions are indicated, in the absence or presence of TMP; SGP5-gsdmD-(GGGS)$_4$-DD-SGP15-IL12-MSA; SGP5-gsdmD-(GGGS)-DD-SGP15-IL12-MSA; SGP5-gsdmD-HL-DD-SGP15-IL12-MSA; SGP5-DD-HL-gsdmD-SGP15-IL12-MSA; SGP5-gsdmD-SGP15-IL12-MSA; No RNA.

DETAILED DESCRIPTION OF CERTAIN EMBODIMENTS

Genetic circuits are partially or fully synthetic genetic assemblages that are designed to perform specific functions. Genetic circuits frequently encompass a series of genes encoded in such a way that the expression of one gene is either increased or decreased by the expression of another, or the expression otherwise depends on certain environmental cues. In this way, genetic circuitry may be designed and considered in a way that is similar to electrical circuitry, consisting of "ON" and "OFF" states, as well as Boolean logic such as "AND" and "OR" logic for the conditions by which output genes are expressed. Genetic circuits are currently the focus of intense study due to the extensive ways in which they might be used, from managing the production of a single chemical to developing entire gene therapies and engineered organisms. Regardless of a circuit's intended application, the ability to accurately control the expression of genes it contains remains of vital importance. This is particularly true in situations where expression must be tightly controlled to ensure that a circuit is effective yet does not synthesize its output to such a degree, timing, location, or duration that the output becomes toxic to a cell or organism.

Genetic circuits have been developed which may be controlled through the presence or absence of small molecules. These circuits have broad applications, such as for expression of cargo genes, temporary expression of immunomodulatory cytokines or antigens for better cancer immunotherapy or vaccination, and for increased safety in use of self-replicating vectors or in combination with other viral-delivery vectors.

Figure 1:
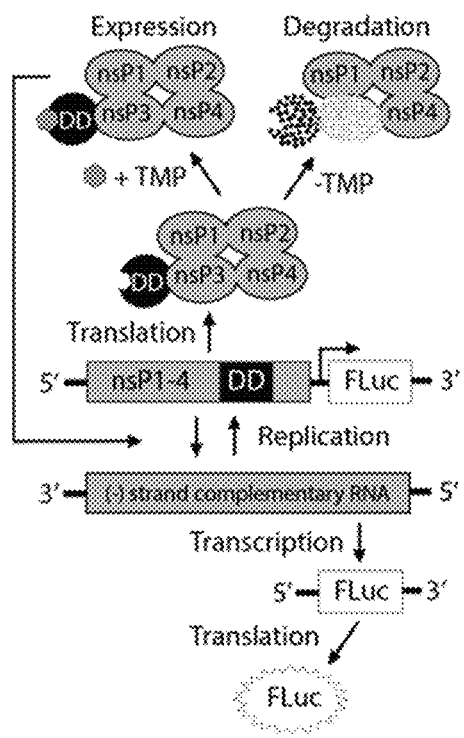
FIG. 1. Schematic illustration of a nsP-DD circuit. nsP-DD fusion proteins are degraded in the absence of a small molecule that stabilizes the DD, TMP. When bound by TMP, nsP-DD fusion proteins are stabilized, allowing nsP1-4 to form a polymerase complex that propagates the replicon, thereby enabling continued expression of its genetic payload.

The genetic circuits described herein are derived from alphavirus replicons which are engineered to allow for controlled expression of one or more encoded cargo genes. The genetic circuits include a set of encoded non-structural proteins (nsPs) which are translated and together form a complex that mediates replication of the circuit in cells. By fusing one of the nsPs with a degradation domain that is stabilized in the presence of a small molecule, replication of the genetic circuit and subsequently expression of its genetic cargo may be controlled in cells by addition or removal of the small molecule (FIG. 1). Such a circuit has a wide range of applications, including a number of therapeutic applications, such as the expression of antigens for vaccination or the expression of cytokines for modulation of the immune system.

Nonstructural Proteins and Replication of Viral Replicons

The present disclosure provides various genetic circuits which are in the form of one or more self-replicating RNA molecules (also referred to herein as "replicons") that are derived from the genome of an alphavirus. The term "alphavirus" refers to any virus belonging to a particular genus of enveloped, positive-sense, single-stranded RNA virus (realm Riboviria; kingdom Orthornavirae; phylum Kitrinoviricota; class Alsuviricetes; order Martellivirales; family Togaviridae; genus Alphavirus), of which approximately 30 species are currently known.

Without wishing to be bound by theory, alphaviruses encode an RNA-dependent RNA polymerase (RdRp) which is sufficient for both replication of the RNA genome and transcription of genes in the genome into messenger RNA. The alphaviral RdRp consists of four nonstructural proteins (nsPs) which are produced as a single polyprotein and are individually referred to as nsP1, nsP2, nsP3, and nsP4. The nsPs encoded by exemplary alphaviruses Venezuelan Equine Encephalitis (VEE) virus and Sindbis virus are provided in SEQ ID NO: 1-4 and SEQ ID NO: 5-8, respectively.

```
Venezuelan equine encephalitis virus nsP1 (SEQ ID NO: 1):
MEKVHVDIEEDSPFLRALQRSFPQFEVEAKQVTDNDHANARAFSHLASKLIETEVDPSDTILDIGSAPAR

RMYSKHKYHCICPMRCAEDPDRLYKYATKLKKNCKEITDKELDKKMKELAAVMSDPDLETETMCLHDDES

CRYEGQVAVYQDVYAVDGPTSLYHQANKGVRVAYWIGFDTTPFMFKNLAGAYPSYSTNWADETVLTARNI

GLCSSDVMERSRRGMSILRKKYLKPSNNVLFSVGSTIYHEKRDLLRSWHLPSVFHLRGKQNYTCRCETIV

SCDGYVVKRIAISPGLYGKPSGYAATMHREGFLCCKVTDTLNGERVSFPVCTYVPATLCDQMTGILATDV

SADDAQKLLVGLNQRIVVNGRTQRNTNTMKNYLLPVVAQAFARWAKEYKEDQEDERPLGLRDRQLVMGCC

WAFRRHKITSIYKRPDTQTIIKVNSDFHSFVLPRIGSNTLEIGLRTRIRKMLEEHKEPSPLITAEDIQEA

KCAADEAKEVREAEELRAALPPLAADFEEPTLEADVDLMLQEAGA

Venezuelan equine encephalitis virus nsP2 (SEQ ID NO: 2):
GSVETPRGLIKVTSYAGEDKIGSYAVLSPQAVLKSEKLSCIHPLAEQVIVITHSGRKGRYAVEPYHGKVV
```

-continued

VPEGHAIPVQDFQALSESATIVYNEREFVNRYLHHIATHGGALNTDEEYYKTVKPSEHDGEYLYDIDRKQ
CVKKELVTGLGLTGELVDPPFHEFAYESLRTRPAAPYQVPTIGVYGVPGSGKSGIIKSAVTKKDLVVSAK
KENCAEIIRDVKKMKGLDVNARTVDSVLLNGCKHPVETLYIDEAFACHAGTLRALTATIRPKKAVLCGDP
KQCGFFNMMCLKVHFNHEICTQVFHKSISRRCTKSVTSVVSTLFYDKRMRTTNPKETKIVIDTTGSTKPK
QDDLILTCFRGWVKQLQIDYKGNEIMTAAASQGLTRKGVYAVRYKVNENPLYAPTSEHVNVLLTRTEDRI
VWKTLAGDPWIKILTAKYPGNFTATIEEWQAEHDAIMRHILERPDPTDVFQNKANVCWAKALVPVLKTAG
IDMTTEQWNTVDYFETDKAHSAEIVLNQLCVRFFGLDLDSGLFSAPTVPLSIRNNHWDNSPSPNMYGLNK
EVVRQLSRRYPQLPRAVATGRVYDMNTGTLRNYDPRINLVPVNRRLPHALVLHHNEHPQSDFSSFVSKLK
GRTVLVVGEKLSVPGKKVDWLSDQPEATFRARLDLGIPGDVPKYDIVFINVRTPYKYHHYQQCEDHAIKL
SMLTKKACLHLNPGGTCVSIGYGYADRASESIIGAIARQFKFSRVCKPKSSHEETEVLFVFIGYDRKART
HNPYKLSSTLTNIYTGSRLHEAGC

Venezuelan equine encephalitis virus nsP3 (SEQ ID NO: 3):
APSYHVVRGDIATATEGVIINAANSKGQPGGGVCGALYKKFPESFDLQPIEVGKARLVKGAAKHIIHAVG
PNFNKVSEVEGDKQLAEAYESIAKIVNDNNYKSVAIPLLSTGIFSGNKDRLTQSLNHLLTALDTTDADVA
IYCRDKKWEMTLKEAVARREAVEEICISDDSSVTEPDAELVRVHPKSSLAGRKGYSTDGKTFSYLEGTK
FHQAAKDIAEINAMWPVATEANEQVCMYILGESMSSIRSKCPVEESEASTPPSTLPCLCIHAMTPERVQR
LKASRPEQITVCSSFPLPKYRITGVQKIQCSQPILFSPKVPAYIHPRKYLVETPPVEETPESPAENQSTE
GTPEQPALVNVDATRTRMPEPIIIEEEEEDSISLLSDGPTHQVLQVEADIHGSPSVSSSSWSIPHASDFD
VDSLSILDTLDGASVTSGAVSAETNSYFARSMEFRARPVPAPRTVFRNPPHPAPRTRTPPLAHSRASSRT
SLVSTPPGVNRVITREELEALTPSRAPSRSASRTSLVSNPPGVNRVITREEFEAFVAQQQRRFDAGA Venezuelan equine encephalitis virus nsP4 (SEQ ID NO: 4):
YIFSSDTGQGHLQQKSVRQTVLSEVVLERTELEISYAPRLDQEKEELLRKKLQLNPTPANRSRYQSRRVE
NMKAITARRILQGLGHYLKAEGKVECYRTLHPVPLYSSSVNRAFSSPKVAVEACNAMLKENFPTVASYCI
IPEYDAYLDMVDGASCCLDTASFCPAKLRSFPKKHSYLEPTIRSAVPSAIQNTLQNVLAAATKRNCNVTQ
MRELPVLDSAAFNVECFKKYACNNEYWETFKENPIRLTEENVVNYITKLKGPKAAALFAKTHNLNMLQDI
PMDRFVMDLKRDVKVTPGTKHTEERPKVQVIQAADPLATADLCGIHRELVRRLNAVLLPNIHTLFDMSAE
DFDAIIAEHFQPGDCVLETDIASFDKSEDDAMALTALMILEDLGVDAELLTLIEAAFGEISSIHLPTKTK
FKFGAMMKSGMFLTLFVNTVINIVIASRVLRERLTGSPCAAFIGDDNIVKGVKSDKLMADRCATWLNMEV
KIIDAVVGEKAPYFCGGFILCDSVTGTACRVADPLKRLFKLGKPLAVDDEHDDDRRRALHEESTRWNRVG
ILPELCKAVESRYETVGTSIIVMAMTTLASSVKSFSYLRGAPITLY Sindbis virus nsP1 (SEQ ID NO: 5):
MEKPVVNVDVDPQSPFVVQLQKSFPQFEVVAQQVTPNDHANARAFSHLASKLIELEVPTTATILDIGSAP
ARRMFSEHQYHCVCPMRSPEDPDRMMKYASKLAEKACKITNKNLHEKIKDLRTVLDTPDAETPSLCFHND
VTCNMRAEYSVMQDVYINAPGTIYHQAMKGVRTLYWIGFDTTQFMFSAMAGSYPAYNTNWADEKVLEARN
IGLCSTKLSEGRTGKLSIMRKKELKPGSRVYFSVGSTLYPEHRASLQSWHLPSVFHLNGKQSYTCRCDTV
VSCEGYVVKKITISPGITGETVGYAVTHNSEGFLLCKVTDTVKGERVSFPVCTYIPATICDQMTGIMATD
ISPDDAQKLLVGLNQRIVINGRTNRNTNTMQNYLLPIIAQGFSKWAKERKDDLDNEKMLGTRERKLTYGC
LWAFRTKKVHSFYRPPGTQTCVKVPASFSAFPMSSVWTTSLPMSLRQKLKLALQPKKEEKLLQVSEELVM
EAKAAFEDAQEEARAEKLREALPPLVADKGIEAAAEVVCEVEGLQADIGA Sindbis virus nsP2 (SEQ ID NO: 6):
ALVETPRGHVRIIPQANDRMIGQYIVVSPNSVLKNAKLAPAHPLADQVKIITHSGRSGRYAVEPYDAKVL
MPAGGAVPWPEFLALSESATLVYNEREFVNRKLYHIAMHGPAKNTEEEQYKVTKAELAETEYVFDVDKKR
CVKKEEASGLVLSGELTNPPYHELALEGLKTRPAVPYKVETIGVIGTPGSGKSAIIKSTVTARDLVTSGK -continued

```
KENCREIEADVLRLRGMQITSKTVDSVMLNGCHKAVEVLYVDEAFACHAGALLALIAIVRPRKKVVLCGD

PMQCGFFNMMQLKVHFNHPEKDICTKTFYKYISRRCTQPVTAIVSTLHYDGKMKTTNPCKKNIEIDITGA

TKPKPGDIILTCFRGWVKQLQIDYPGHEVMTAAASQGLTRKGVYAVRQKVNENPLYAITSEHVNVLLTRT

EDRLVWKTLQGDPWIKQPTNIPKGNFQATIEDWEAEHKGIIAAINSPTPRANPFSCKTNVCWAKALEPIL

ATAGIVLTGCQWSELFPQFADDKPHSAIYALDVICIKFFGMDLTSGLFSKQSIPLTYHPADSARPVAHWD

NSPGTRKYGYDHAIAAELSRRFPVFQLAGKGTQLDLQTGRTRVISAQHNLVPVNRNLPHALVPEYKEKQP

GPVKKFLNQFKHHSVLVVSEEKIEAPRKRIEWIAPIGIAGADKNYNLAFGFPPQARYDLVFINIGTKYRN

HHFQQCEDHAATLKTLSRSALNCLNPGGTLVVKSYGYADRNSEDVVTALARKFVRVSAARPDCVSSNTEM

YLIFRQLDNSRTRQFTPHHLNCVISSVYEGTRDGVGA

Sindbis virus nsP3 (SEQ ID NO: 7):
APSYRTKRENIADCQEEAVVNAANPLGRPGEGVCRAIYKRWPTSFTDSATETGTARMTVCLGKKVIHAVG

PDFRKHPEAEALKLLQNAYHAVADLVNEHNIKSVAIPLLSTGIYAAGKDRLEVSLNCLTTALDRTDADVT

IYCLDKKWKERIDAALQLKESVTELKDEDMEIDDELVWIHPDSCLKGRKGFSTTKGKLYSYFEGTKFHQA

AKDMAEIKVLFPNDQESNEQLCAYILGETMEAIREKCPVDHNPSSSPPKTLPCLCMYAMTPERVHRLRSN

NVKEVTVCSSTPLPKHKIKNVQKVQCTKVVLFNPHTPAFVPARKYIEVPEQPTAPPAQAEEAPEVVATPS

PSTADNTSLDVTDISLDMDDSSEGSLFSSFSGSDNSITSMDSWSSGPSSLEIVDRRQVVVADVHAVQEPA

PIPPPRLKKMARLAAARKEPTPPASNSSESLHLSFGGVSMSLGSIFDGETARQAAVQPLATGPTDVPMSF

GSFSDGEIDELSRRVTESEPVLFGSFEPGEVNSIISSRSAVSFPLRKQRRRRRSRRTEY

Sindbis virus nsP4 (SEQ ID NO: 8):
LTGVGGYIFSTDTGPGHLQKKSVLQNQLTEPTLERNVLERIHAPVLDTSKEEQLKLRYQMMPTEANKSRY

QSRKVENQKAITTERLLSGLRLYNSATDQPECYKITYPKPLYSSSVPANYSDPQFAVAVCNNYLHENYPT

VASYQITDEYDAYLDMVDGTVACLDTATFCPAKLRSYPKKHEYRAPNIRSAVPSAMQNTLQNVLIAATKR

NCNVTQMRELPTLDSATFNVECFRKYACNDEYWEEFARKPIRITTEFVTAYVARLKGPKAAALFAKTYNL

VPLQEVPMDRFVMDMKRDVKVTPGTKHTEERPKVQVIQAAEPLATAYLCGIHRELVRRLTAVLLPNIHTL

FDMSAEDFDAIIAEHFKQGDPVLETDIASFDKSQDDAMALTGLMILEDLGVDQPLLDLIECAFGEISSTH

LPTGTRFKFGAMMKSGMFLTLFVNTVLNVVIASRVLEERLKTSRCAAFIGDDNIIHGVVSDKEMAERCAT

WLNMEVKIIDAVIGERPPYFCGGFILQDSVTSTACRVADPLKRLFKLGKPLPADDEQDEDRRRALLDETK

AWFRVGITGTLAVAVTTRYEVDNITPVLLALRTFAQSKRAFQAIRGEIKHLYGGPK
```

Amino acid sequences for the nsPs of VEE virus and Sindbis virus may also be found via the following accession numbers from the U.S. National Center for Biotechnology Information (NCBI): NP_740696.1, NP_740697.1, NP_740698.1, NP_740699.1, NP_740670.1, NP_740671.1, NP_740672.1, and NP_740669.1, which are incorporated by reference herein. Amino acid sequences for the entire nsP polyprotein of VEE virus and Sindbis virus may be found via accession numbers NP_040822.1 and NP_062888.1, which are incorporated by reference herein.

Nucleotide sequences encoding the nsP polyproteins of VEE virus and Sindbis virus may be found via accession numbers NC_001449.1 (nucleobases 45-7526) and NC_001547.1 (nucleobases 60-7601), which are incorporated by reference herein.

The present disclosure provides engineered (i.e., recombinant) replicons encoding a nsP1, nsP2, nsP3, and nsP4 (nsP1-4) genes. In some embodiments, one or more of nsP1-4 genes are derived from VEE virus. In some embodiments, one or more of nsP1-4 genes are derived from Sindbis virus. In further embodiments, one or more of nsP1-4 genes are derived from another alphavirus such as, but not limited to, Eastern Equine Encephalitis virus, the Highlands J virus, the Middelburg virus, the Ross River virus, the Semliki Forest virus, or the Western Equine Encephalitis virus.

In some embodiments, each of the nsP1-4 genes are derived from the same alphavirus. In some embodiments, any two or more of nsP1-4 genes are derived from different alphaviruses.

In some embodiments, the nsP1-4 genes are transcribed as a single transcript, yielding a polyprotein when translated. In some embodiments, the nsP1-4 genes are transcribed as separate transcripts, yielding separate proteins when translated.

In some embodiments, nsP1-4 are the only alphaviral genes encoded by a replicon, i.e., the replicon lacks any other alphaviral gene, such as those encoding structural proteins (e.g., core nucleocapsid protein C, envelope protein P62, and envelope protein E1). In such an embodiment, the replicon is incapable of producing a viral particle as it is incapable of synthesizing a viral capsid.

In some embodiments, one or more genes encoding nsP1-4 comprise mutations compared to the corresponding wild-type (i.e., native) sequence. A mutation is defined as a change in one or more nucleobases of a given nucleotide sequence relative to the wild-type sequence. In embodiments concerning an alphavirus-derived replicon, a mutation refers to a change in one or more nucleobases of the single-stranded RNA nucleotide sequence. A mutation may comprise the insertion, deletion, or substitution of one or more nucleobases. A mutation may change the stability of an mRNA transcript transcribed from a given sequence relative to an mRNA transcript transcribed from the wild-type sequence, causing the transcript to become either more or less susceptible to degradation. A mutation may also cause an mRNA transcript transcribed from a given sequence to become either more or less codon optimized than the wild-type sequence, meaning that the mutant mRNA is either more or less readily translated into protein by a particular organism. A mutation may alter one or more amino acids encoded by a given sequence or an mRNA transcript transcribed from it. A mutation that alters one or more amino acids of a translated protein (e.g., nsP1-4) may change the 3-dimensional structure and/or folding kinetics of the mutated protein relative to the wild-type protein. A mutation that alters one or more amino acids of a translated protein may change the activity of the mutated protein relative to the wild-type protein and/or cause the mutated protein to become either more or less susceptible to degradation relative to the wild-type protein.

In some embodiments, mutations are contemplated that comprise the insertion of one or more proteins or peptides into the reading frame of one or more genes, such that when these genes are transcribed and translated, they result in a fusion protein comprising multiple proteins and/or peptides which are covalently linked together by peptide bonds. The fusion of one protein with another protein or peptide may confer additional activities or functions to the original protein. In some embodiments, for example, the proteins to be fused are an nsP (e.g., nsP1, nsP2, nsP3, or nsP4) and a destabilization domain (DD), in such a way as to confer the properties of the destabilization domain to the nsP.

A fusion protein may further comprise one or more peptide linkers between the proteins it comprises, which may, for example, enhance the folding and/or function of each protein connected by the one or more linkers. A linker may be flexible (i.e., unstructured) or rigid (i.e., having a secondary structure, such as an α-helical structure). A linker may be short, having a length of about 4 amino acids or fewer, or long, having a length of about 5 amino acids or more. A flexible linker may consist primarily of a sequence that is glycine-rich (e.g., GGGS (SEQ ID NO: 12)), which may be a repeating sequence. A linker may contain no site that is targeted by a known protease (i.e., an uncleavable linker), such that the fused proteins cannot be separated from one another when expressed in a cell.

In some embodiments, the RNA molecule(s) of the genetic circuit are encoded on one or more RNA replicons. In such embodiments, genes comprised by the one or more RNA molecule(s) may be expressed from one or more subgenomic promoters of the one or more replicons. In some embodiments, expression from the one or more subgenomic promoters are regulated by a small molecule, such as trimethoprim (TMP). In some embodiments, a small molecule regulates expression from one or more subgenomic promotors by interacting directly with and stabilizing a destabilization domain that is fused to a protein produced by expression of the one or more subgenomic promotors (e.g., an nsP or an output protein), thereby increasing the intracellular level of the protein.

In some embodiments, the RNA molecule(s) of the genetic circuit includes modified RNA. Such modified RNA molecules can include, for example, modified nucleotides such as, but not limited to, 5-methylcytosine-triphosphate, pseudouridine-triphosphate, 2-aminopurine-triphosphate, 5-bromo-uridine-triphosphate, inosine-triphosphate, 7-methylguanosine-triphosphate, 2'-O-methyl ribonucleotide analogs, and 2'-fluoro ribonucleotide analogs. Modified RNA molecules may also include, for example, non-ribonucleotides (e.g., deoxyribonucleotides), locked nucleic acid (LNA) nucleotides comprising a methylene bridge between the 2' and 4' carbons of the ribose ring, and bridged nucleic acids (BNA), or backbone modifications such as phosphorothioate. Other modifications of RNA molecules are known in the art, and may be useful, for example, to increase stability or resistance of the RNA molecule(s) to RNases.

Destabilization Domains and Fusion Proteins Thereof

Particularly contemplated herein are genetic circuits comprising one or more RNA molecule(s) that encode fusion proteins containing one or more destabilization domains. A destabilization domain (DD) is an amino acid sequence that is readily identified and degraded by one or more components of protein quality control machinery within cells of a particular organism, such as, but not limited to, the ubiquitin proteosome system of eukaryotes. A destabilization domain may also be referred to as a "degron" or "degradation domain". A destabilization domain may be a complete protein or a subset of a protein (e.g., an amino acid sequence corresponding to one or more domains within a protein, or part of a domain thereof).

In some embodiments, one or more proteins encoded by a genetic circuit are fused with a destabilization domain. In such embodiments, fusion with a destabilization domain causes the one or more fused proteins to be targeted by degradation machinery within cells, thereby decreasing their intracellular quantity. In some embodiments, one or more of nsP1, nsP2, nsP3, and nsP4 are fused with a destabilization domain. In such embodiments, the genetic circuit comprises genes encoding these proteins in which a mutation has been made to insert a nucleotide sequence encoding the destabilization domain. Such a mutation is made such that the inserted sequence encoding the destabilization domain is in frame with the nucleotide sequence encoding the protein (e.g., nsP1, nsP2, nsP3, or nsP4), such that when the sequence is transcribed and translated, a fusion protein comprising both the original protein and the destabilization domain is produced. In embodiments where one or more nsPs are fused with a destabilization domain, the RdRp complex consisting of nsP1-4 cannot be efficiently formed. As a result, replication of the genetic circuit and expression of the genes it contains are decreased. The destabilization domain may be stabilized in the presence of a small molecule that interacts directly with the stabilization domain, thereby stabilizing the fused nsP such that functional RdRp complexes are able to be efficiently formed.

In some embodiments, the destabilization domain to be fused with one or more proteins of the genetic circuit (e.g., nsP1, nsP2, nsP3, or nsP4) is a destabilization domain derived from the dihydrofolate reductase (DHFR) of *Escherichia coli* (DDd). The development of DDds comprising various mutations relative to wild-type *E. coli* DHFR is well known in the art (see, e.g., Iwamoto et al. (2010). "A general chemical method to regulate protein stability in the mammalian central nervous system" *Chem Biol,* 17(9), 981-988, which is incorporated by reference herein). Such mutations are well known to, for instance, modify the folding of DHFR and therefore its susceptibility to protein degradation. The small-molecule ligand trimethoprim (TMP) and derivatives thereof stabilize DDd in a rapid, reversible, and dose-dependent manner. For reference, the amino acid sequence of *E. coli* strain K-12 DHFR comprising R12H and G67S mutations, upon which many DHFR variants are based, is provided in SEQ ID NO: 9.

```
E. coli dihydrofolate reductase destabilization
domain (SEQ ID NO: 9):
MISLIAALAVDHVIGMENAMPWNLPADLAWFKRNTLNKPVIMGRHTWESI

GRPLPGRKNIILSSQPSTDDRVTWVKSVDEAIAACGDVPEIMVIGGGRVY

EQFLPKAQKLYLTHIDAEVEGDTHFPDYEPDDWESVFSEFHDADAQNSHS

YCFEILERR
```

In some embodiments, the destabilization domain to be fused with one or more proteins of the genetic circuit (e.g., nsP1, nsP2, nsP3, or nsP4) is a destabilization domain derived from the ligand binding domain of human estrogen receptor (DDe). The development of DDes comprising various mutations relative to wild-type human estrogen receptor ligand binding domain is well known in the art (see, e.g., Miyazaki et al. (2012) "Destabilizing domains derived from the human estrogen receptor" *J Am Chem Soc*, 134(9):3942-5, which is incorporated by reference herein). Such mutations are well known to, for instance, modify the folding of the ligand binding domain and therefore its susceptibility to protein degradation. The small-molecule ligands CMP8 or 4-hydroxytamoxifen (4-OHT) and derivatives thereof stabilize DDe in a rapid, reversible, and dose-dependent manner. For reference, the amino acid sequence of *Homo sapiens* estrogen receptor ligand binding domain comprising T371A, L384M, M421G, N519S, G521R, and Y537S mutations, upon which many estrogen receptor ligand binding domain variants are based, is provided in SEQ ID NO: 10.

```
H. sapiens estrogen receptor ligand binding domain
destabilization domain (SEQ ID NO: 10):
SLALSLTADQMVSALLDAEPPILYSEYDPTRPFSEASMMGLLTNLADREL

VHMINWAKRVPGFVDLALHDQVHLLECAWMEILMIGLVWRSMEHPGKLLF

APNLLLDRNQGKCVEGGVEIFDMLLATSSRFRMMNLQGEEFVCLKSIILL

NSGVYTFLSSTLKSLEEKDHIHRVLDKITDTLIHLMAKAGLTLQQQHQRL

AQLLLILSHIRHMSSKRMEHLYSMKCKNVVPLSDLLLEMLDAHRL
```

In some embodiments, the destabilization domain to be fused with one or more proteins of the genetic circuit (e.g., nsP1, nsP2, nsP3, or nsP4) is a destabilization domain derived from the human FK506 binding protein (FKBP) (DDf). The development of DDfs comprising various mutations relative to wild-type human FKBP is well known in the art (see, e.g., Banaszynski et al. (2006) "A rapid, reversible, and tunable method to regulate protein function in living cells using synthetic small molecules" *Cell*, 126(5), 995-1004, which is incorporated by reference herein). Such mutations are well known to, for instance, modify the folding of FKBP and therefore its susceptibility to protein degradation. The small-molecule ligand Shield-1 and derivatives thereof stabilize DDf in a rapid, reversible, and dose-dependent manner. For reference, the amino acid sequence of *Homo sapiens* FKBP comprising a F36V mutation, upon which many FKBP variants are based, is provided in SEQ ID NO: 11.

```
FK506 binding protein destabilization domain
(SEQ ID NO: 11):
MGVQVETISPGDGRTFPKRGQTCVVHYTGMLEDGKKVDSSRDRNKPFKFM

LGKQEVIRGWEEGVAQMSVGQRAKLTISPDYAYGATGHPGIIPPHATLVF

DVELLKLE
```

In further embodiments, a destabilization domain is fused to one or more proteins encoded by the genetic circuit other than nsP1-4. In such embodiments, a protein fused to a destabilization domain may be one or more proteins encoded by an output gene of the genetic circuit. In such embodiments, one or more output proteins fused to a destabilization domain may further regulate expression of one or more genes of the genetic circuit.

In some embodiments, a destabilization domain fused to an output protein is the same type of destabilization domain as that fused to one or more nsPs. In some embodiments, a destabilization domain fused to an output protein is different than that fused to one or more nsPs.

Small Molecules

In some embodiments, a destabilization domain comprised by one or more proteins encoded by the genetic circuit is stabilized in the presence of one or more molecules, such that the susceptibility of the protein to components of protein degradation machinery is reduced. In some embodiments, the molecule is a small molecule, generally understood in the art to be any molecule with a molecular mass of less than 900 daltons. In some embodiments, a small molecule is cell permeable. In some embodiments, addition of a small molecule to a cell comprising a genetic circuit encoding a fusion protein comprising a destabilization domain causes the intracellular level of the fusion protein to increase relative to the absence of the small molecule. In such embodiments, the intracellular level of the fusion protein may be increased by 10%, increased by 20%, increased by 30%, increased by 40%, increased by 50%, increased by 60%, increased by 70%, increased by 80%, increased by 90%, increased by 100%, increased by 125%, increased by 150%, increased by 175%, increased by 200%, increased by 250%, increased by 300%, increased by 350%, increased by 400%, increased by 450%, increased by 500%, increased by 600%, increased by 700%, increased by 800%, increased by 900%, or increased by 1000% or more.

In some embodiments, the small molecule directly interacts (i.e., binds) with the destabilization domain. In some embodiments, interaction with the small molecule enhances folding of the destabilization domain. In some embodiments, interaction with the small molecule prevents recognition of the destabilization domain by components of protein degradation machinery. In some embodiments, the interaction between the destabilization domain and the small molecule may be characterized in terms of a dissociation constant ($K_D$). In such embodiments, the small molecule interacts with a destabilization domain with a $K_D$ of at least 10 pM, at least 20 pM, at least 30 pM, at least 40 pM, at least 50 pM, at least 60 pM, at least 70 pM, at least 80 pM, at least 90 pM, at least 100 pM, at least 125 pM, at least 150 pM, at least 175 pM, at least 200 pM, at least 250 pM, at least 300 pM, at least 350 pM, at least 400 pM, at least 450 pM, at least 500 pM, at least 600 pM, at least 700 pM, at least 800 pM, at least 900 pM, at least 1 nM, at least 10 nM, at least 25 nM, at least 50 nM, at least 75 nM, at least 100 nM, at least 125 nM, at least 150 nM, at least 175 nM, at least 200 nM, at least 250 nM, at least 300 nM, at least 350 nM, at least 400 nM, at least 450 nM, at least 500 nM, at least 600 nM, at least 700 nM, at least 800 nM, at least 900 nM, or at least 1 μM.

In some embodiments where at least one destabilization domain comprised by a fusion protein encoded by the genetic circuit is an *E. coli* dihydrofolate reductase (DHFR) destabilization domain (DDd), the small molecule is trimethoprim (TMP) or a derivative thereof. Derivatives of trimethoprim are compounds that would generally be understood by those well versed in the art to share structural features of trimethoprim and include, for instance, iodinated trimethoprim (TMP-I) and diaveridine (see, e.g., Nilchan et al. (2018) "Halogenated trimethoprim derivatives as multi-drug-resistant *Staphylococcus aureus* therapeutics" *Bioorg Med Chem*, 26(19):5343-5348, which is incorporated by reference herein). The use of trimethoprim and derivatives thereof to reduce degradation of proteins containing a DDd is well known in the art, for example, in Iwamoto et al. (2010). "A general chemical method to regulate protein stability in the mammalian central nervous system" *Chem Biol*, 17(9), 981-988, which is incorporated by reference herein.

In some embodiments where at least one destabilization domain comprised by a fusion protein encoded by the genetic circuit is a human estrogen receptor ligand binding domain destabilization domain (DDe), the small molecule is 4-hydroxytamoxifen (4-OHT) or a derivative thereof. Derivatives of 4-hydroxytamoxifen are compounds that would generally be understood by those well versed in the art to share structural features of 4-hydroxytamoxifen and include, for example, endoxifen (see, e.g., Maximov et al. (2018) "Endoxifen, 4-Hydroxytamoxifen and an Estrogenic Derivative Modulate Estrogen Receptor Complex Mediated Apoptosis in Breast Cancer" *Mol Pharmacol*, 94(2), 812-822, which is incorporated by reference herein). The use of 4-hydroxytamoxifen and derivatives thereof to reduce degradation of proteins containing a DDe is well known in the art, for example, in Miyazaki et al. (2012) "Destabilizing domains derived from the human estrogen receptor" *J Am Chem Soc*, 134(9):3942-5, which is incorporated by reference herein.

In some embodiments where at least one destabilization domain comprised by a fusion protein encoded by the genetic circuit is a human FK506 binding protein (FKBP) destabilization domain (DDf), the small molecule is a Shield ligand or a derivative thereof. A Shield ligand may be, for example, Shield-1 or Shield-2 (see, e.g., Grimley et al. (2008) "Synthesis and analysis of stabilizing ligands for FKBP-derived destabilizing domains". *Bioorg Med Chem Lett*, 18(2), 759-761, which is incorporated by reference herein), or a derivative compound that would generally be understood by those well versed in the art to share structural features of Shield-1 or Shield-2. The use of Shield ligands to reduce degradation of proteins containing a DDf is well known in the art, for example, in Banaszynski et al. (2006) "A rapid, reversible, and tunable method to regulate protein function in living cells using synthetic small molecules". *Cell*, 126(5), 995-1004, which is incorporated by reference herein.

Output Genes

In some embodiments, the genetic circuit further encodes one or more output genes from which one or more output molecules are produced when expressed. An output gene may also be referred to as a cargo gene. In some embodiment, an output molecule is a protein. However, in other embodiments the output molecule may be another type of molecule, such as a nucleic acid molecule (e.g., a DNA or RNA), for example an RNA molecule that is an input for a strand displacement reaction, or a micro-RNA (miRNA) molecule that functions in post-transcriptional silencing of gene expression. Protein output molecules may include therapeutic proteins, cell death proteins, marker proteins, fluorescent proteins, luminescent proteins, antigen proteins (and/or adjuvants), selection proteins, RNA-binding proteins, enzymes, and immunomodulators.

Therapeutic proteins can be any protein that is used in therapy of disease. For example, a therapeutic protein can be a protein used for protein replacement therapy, such as for metabolic disorders; Myr-Akt for treating Duchenne muscular dystrophy; or follistatin for treating Becker muscular dystrophy, Duchenne muscular dystrophy, or inclusion body myositis.

Selection proteins can be used for selection or purification of a cell in which the selection protein is expressed. For example, the selection protein can be a protein that confers drug resistance to a cell, or acts as a marker for the cell type for separation from other cells by separation techniques such as flow cytometry.

Exemplary marker proteins include fluorescent proteins, which include many different types of proteins known in the art, such as, for example, enhanced green fluorescent protein (EGFP), enhanced yellow fluorescent protein (EYFP), enhanced blue fluorescent protein (EBFP), cyan fluorescent proteins (e.g., AmCyan1), other green fluorescent proteins (e.g., AcGFP1, and ZsGreen1), other yellow fluorescent proteins (e.g., mVenus, ZsYellow1 and mBananna), orange fluorescent proteins (e.g., mOrange and mOrange2), red fluorescent proteins (e.g., DsRed, tdTomato, mStrawberry and mCherry), and far-red fluorescent proteins (e.g., mKate, HcRedl, mRaspberry and mPlum). Exemplary marker proteins also include luminescent proteins, which include many different types of proteins known in the art, such as, for example, firefly (*Photinus pyralis*) luciferase, sea pansy (*Renilla reniformis*) luciferase, and derivative luminescent reporter enzymes thereof.

Antigen proteins include, for example, proteins of infectious agents or cancer antigens, of which many are known in the art. An antigen protein may be, for example, a viral antigen, such as a human immunodeficiency virus (HIV) antigen. Protein adjuvants also can be expressed, alone or in conjunction with antigen output proteins.

Immunomodulator proteins include cytokines, for example, IL-2, IL-12, IL-15 or IL-21, or immunosuppressant proteins.

Cell death proteins include, for example, hBax, Herpes simplex virus thymidine kinase (TK), gasdermin D, or gasdermin E, which kill cells through apoptosis or pyroptosis.

In some embodiments, the genetic circuits described herein include RNA molecules that encode more than one type of output molecule.

An output molecule protein may also be a protein that specifically binds to an RNA motif and may therefore be used to further control expression of other output genes comprised by the genetic circuit. Proteins that specifically bind to an RNA motif and inhibit protein production by a variety of mechanisms including repression of translation or degradation of RNA are included in many of the embodiments of the genetic circuits described herein. Such proteins may be referred to herein as a "protein that specifically binds to an RNA motif and inhibits protein production" or an "RNA binding protein" or the like. Such RNA binding proteins bind to a specific RNA sequence (also referred to as a "RNA motif" herein) and inhibit protein production by repressing translation of the RNA molecule to which they bind. Repression of translation can occur any of the several mechanisms known in the art for repression of translation. Alternatively, such RNA binding proteins bind to a specific RNA sequence (also referred to as a "RNA motif" herein) and inhibit protein production by degradation of RNA.

One example of a protein that specifically binds to an RNA motif and inhibits protein production is L7Ae. The L7Ae protein binds to one or more Box C/D, K-turn and/or K-loop motifs in an RNA molecule. In some embodiments more than one Box C/D, K-turn and/or K-loop motifs (such as two K-turn motifs) are included in an RNA molecule to confer better binding to the RNA molecule and repression of RNA translation. In some embodiments, the one or more Box C/D, K-turn and/or K-loop motifs are placed in the 5' untranslated region (UTR) of the RNA molecule, i.e., upstream of a sequence encoding an output molecule. In addition, other proteins that bind specific RNA motifs and inhibit protein production can be used in the same manner as described herein for L7Ae.

Another example of a protein that specifically binds to an RNA motif and inhibits protein production is a fusion of MS2 protein and a protein that degrades RNA. In some embodiments, MS2 protein can be fused to CNOT7 protein (to form MS2-CNOT7) or Dm-POP2 protein (to form MS2-Dm-POP2), each of which are deadenylases, but other proteins that degrade RNA also can be fused or linked to MS2. In addition, other proteins that bind to specific RNA motifs but do not repress translation can be fused to a protein that degrades RNA and used in the same manner as described herein for MS2-CNOT7.

MS2 protein binds to one or more MS2 coat protein binding sites. In some embodiments more than one MS2 coat protein binding sites (such as eight MS2 coat protein binding sites) are included in an RNA molecule to confer better binding to the RNA molecule and inhibition of protein production, e.g., by degradation of the RNA. In some embodiments, the one or more MS2 coat protein binding sites are placed in the 3' untranslated region (UTR) of the RNA molecule, i.e., downstream of a sequence encoding an output molecule.

In some additional embodiments, the output molecule is a fusion protein. In some embodiments, such an output molecule may be a fusion protein comprising a destabilization domain, such as DDd, DDe, or DDf, that may be the same or different destabilization domain as that comprised by one or more of nsP1-4 encoded by the genetic circuit.

In other embodiments, the output may be a fusion protein comprising a tetracycline repressor (TetR) protein. In such embodiments, the genetic circuit may comprise one or more RNA molecules which further include an aptamer sequence and an additional gene encoding a one or more separate output molecules, wherein the aptamer sequence is bound by the TetR protein in the absence of tetracycline. The aptamer sequence may be positioned in proximity to the gene, such that expression of the one or more separate output molecules is inhibited in the absence of tetracycline due to binding of TetR to the aptamer sequence. In some embodiments, a fusion protein comprising TetR also comprises a second protein that enhances binding of TetR to the aptamer sequence, such as DDX6. Use of TetR-DDX6 to regulate gene expression is well known in the art, for example in Ganesan et al. (2016) "Synthetic RNA-protein modules integrated with native translation mechanisms to control gene expression in malaria parasites", *Nat Commun* 7, 10727, which is incorporated by reference herein.

Methods of Treatment

Also provided are methods for treating or preventing disease using the genetic circuits described herein. In some embodiments, methods of treating cancer in a mammal are provided, in which a genetic circuit comprising one or more RNA molecules is administered to a mammal. In some embodiments, a genetic circuit produces an output protein that treats the cancer, including but not limited to a cell death protein such as hBax or gasdermin D, or an immunomodulatory protein such as a cytokine (e.g., IL-12, IL-15, IL-21).

Also provided are methods for inducing an immune response in a mammal using the synthetic RNA circuits described herein. In some embodiments, the methods include administering to a subject a genetic circuit comprising one or more RNA molecules, which produces one or more output proteins that induces the immune response or augments the immune response. Such methods may be used in vaccination of a mammal, or for other uses in which inducing an immune response is beneficial to the mammal. The output protein produced typically is one or more antigens (e.g., a protein antigen or a nucleic acid antigen), but may also include one or more adjuvants, and/or other immunomodulatory proteins.

In some embodiments, the methods also include controlling the expression of the output molecule(s) by administering molecules (e.g., small molecules) that control destabilization domains (e.g., trimethoprim, 4-hydroxytamoxifen, Shield ligands) or that control binding of TetR protein to aptamers (e.g., tetracycline). In some embodiments, the genetic circuit described herein may be administered to a subject at one time, followed by subsequent administration of molecules that control expression of the output molecules (s) at a different time. Such administration of the genetic circuits described herein and molecules that control expression of the output molecules(s) and/or replication of the genetic circuit in cells can be used to express antigens and/or adjuvants at certain times relative to one another in order to produce an improved immune response in the subject, compared to in the absence of the genetic circuit. Molecules (e.g., small molecules) that control expression of the output molecules(s) may be administered by any suitable method including, but not limited to, oral administration, intramuscular injection of lipid nanoparticles, or implantation of a polymeric implant for sustained release.

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

Certain embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

Example 1. Design and Synthesis of DD-nsP2 and nsP3-DD Genetic Circuits

Self-replicating RNAs (replicons) derived from alphaviruses are an emerging technology, widely recognized for their potential in vaccination and cancer immunotherapy [1-9]. Precise control of replicon behavior, such as replication and payload expression, plays a critical role in the development of improved efficacy in both vaccinations and cancer therapy applications.

Though replication and payload expression are mainly determined by the activity of non-structural viral proteins (nsP1-4), which perform the essential enzymatic reactions such as RNA-dependent RNA polymerization and 5' capping of the replicon RNA [10, 11], the focus of replicon engineering so far has been in subgenomic promoter design and RNA-binding protein based-regulation [12,13]. Fewer efforts on nsP1-4 engineering to manipulate the behaviors of replicon RNA have been reported, most notably the generation of noncytopathic replicons [14] and in vitro evolution (IVE) of replicons [15].

Figure 2:
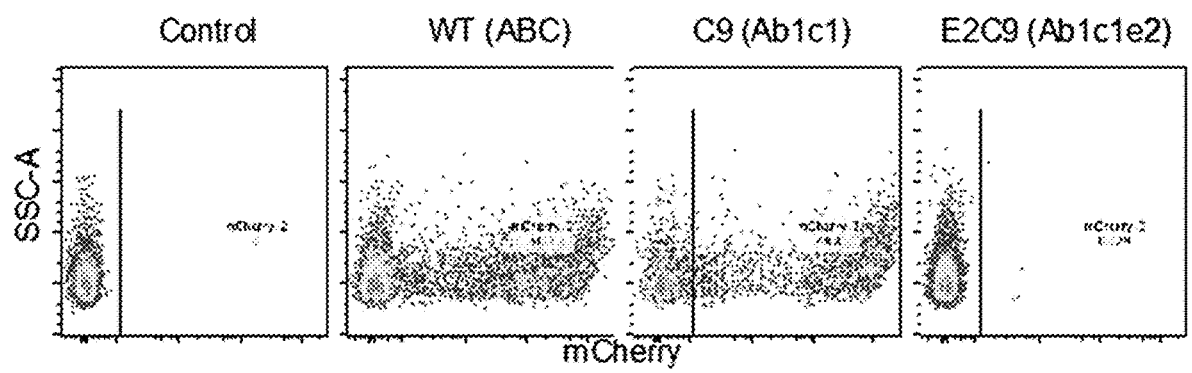
FIG. 2. Dead replicon (Ab1c1e2, E2C9) with a point mutation in nsP2 does not express cargo reporter mCherry. Shown are FACS plots of mCherry expression (X-axis) versus SSC-A (Y-axis) in B16F10 cells at 1 day post transfection with wildtype (WT (ABC)), C9 (Ab1c1), and E2C9 (Ab1c1e2) mCherry-encoding replicon RNA by lipofectamine.

A point mutation in the protease nsP2 was identified that results in a failure of the replicon to express the reporter cargo protein mCherry (FIG. 2). Interestingly, other mutations identified by IVE experiments also localize to a compact structure in nsP2 and nsP3 [15].

Figure 3A:
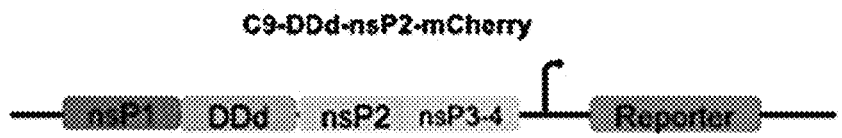
FIGS. 3A-3C. DDd-nsP2 expresses cargo genes in response to TMP.
Figure 3B:
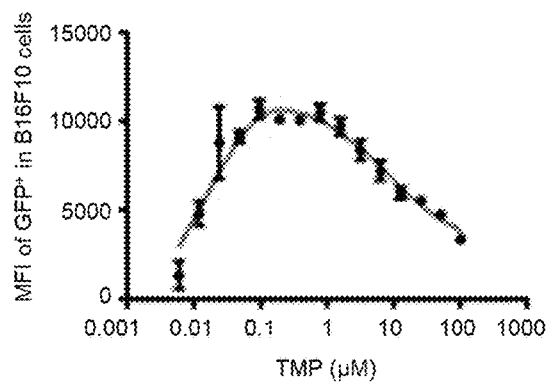
Figure 3C:
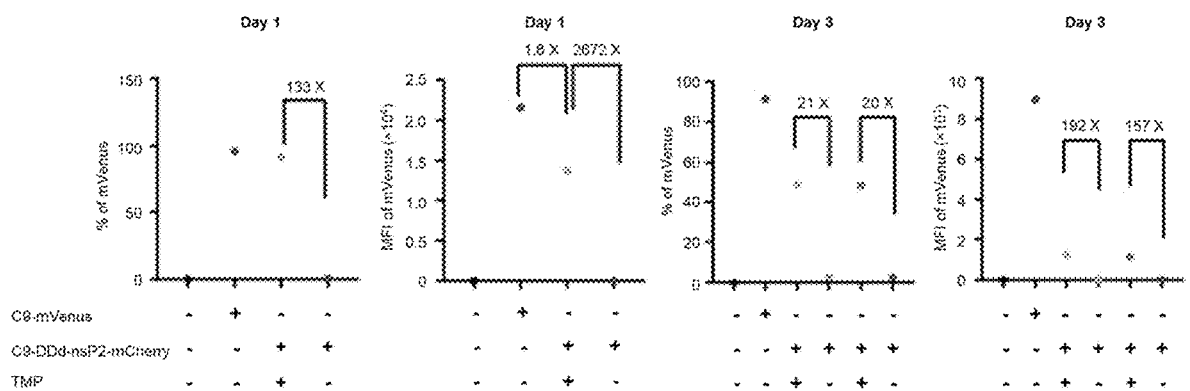
Figure 4A:
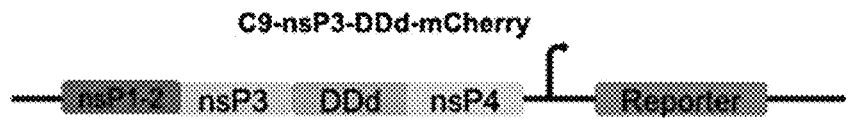
FIG. 4A-4D. nsP3-DDd expresses cargo genes in responses to TMP.
Figure 4B:
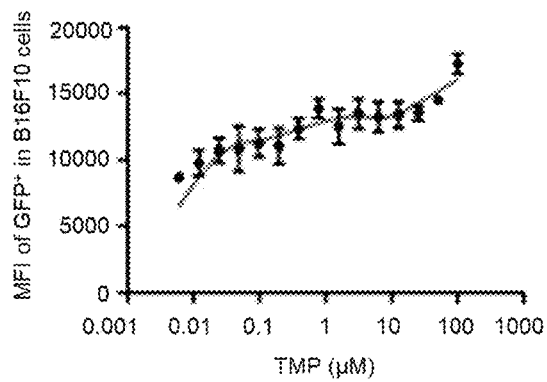
Figure 4C:
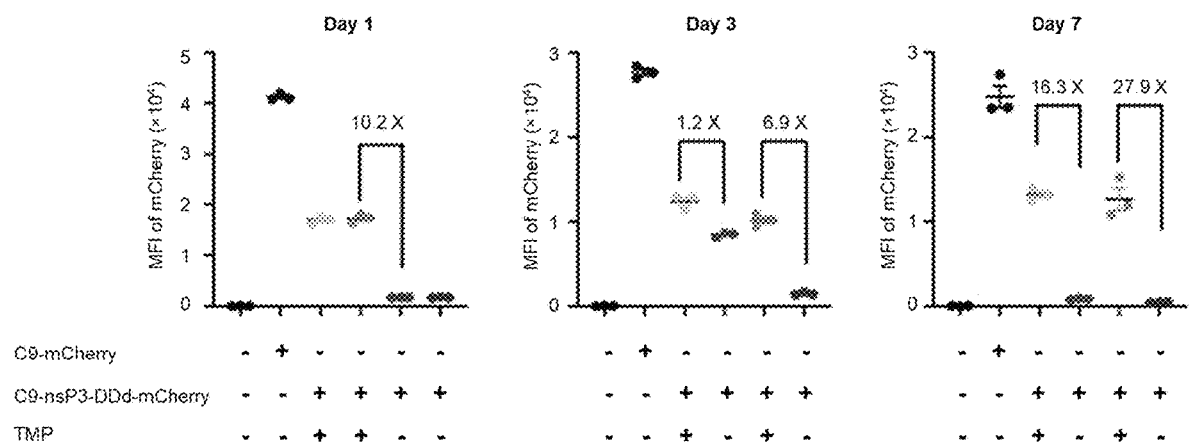
Figure 4D:
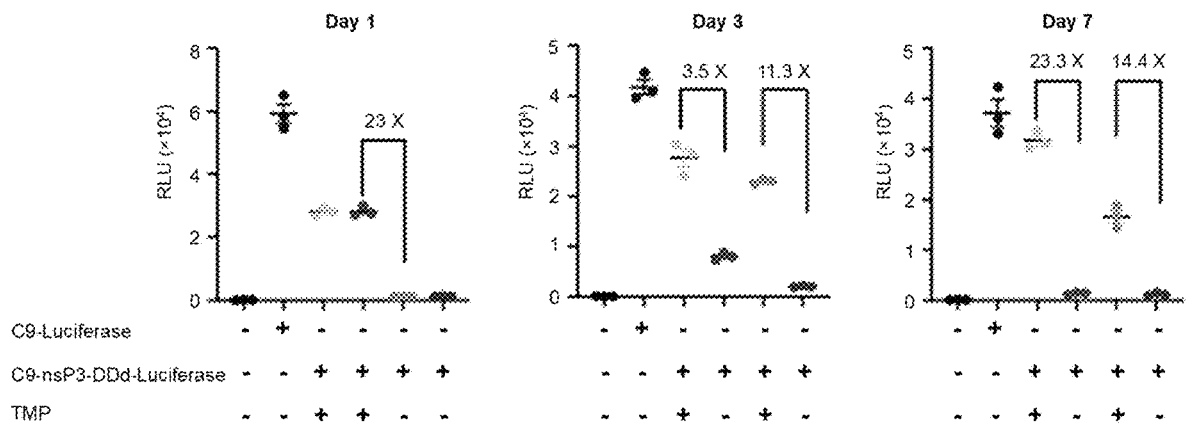

These data suggested the possibility to regulate replicon replication and cargo expression through modification of nsP2 and nsP3, which would allow small molecule-responsive modulation of protein stability and function. To demonstrate this, nsP2 and nsP3 were tagged with an *E. coli* DHFR-derived destabilization domain (DDd) [13, 16] on their N- and C-terminus respectively. Replicon RNA with an N-terminally tagged DDd-nsP2 expresses the reporter cargo (GFP) only in presence of trimethoprim (TMP). Treatment with TMP immediately after transfection results in percentage of positive cells comparable to transfection with wild type replicon, while fluorescence levels are dose dependent on TMP. Treating the transfected cells one day post transfection results in around 10% of cells expressing GFP in response to TMP (FIGS. 3A-3C).

Similarly, replicon with C-terminally tagged nsP3-DDd also expresses reporter in responses to TMP, but with significant leakage in absence of TMP. Interestingly, this design allows an increase in reporter expression in response to TMP in a much higher percent of cell population even when TMP is added one day post transfection. In response to TMP addition or removal, reporter expression showed fast turn-on and slow turn-off kinetics, respectively (FIGS. 4A-4D).

Taken together, DDd-nsP2 is a good genetic circuit for systems that require a tight off state and could serve as a kill switch upon TMP removal. On the other hand, nsP3-DDd is suitable as an on-switch or slow off-switch in situations where leaky expression can be tolerated but protein level modulation is required over a longer period, for example in expression of antigens in a vaccine application.

In summary, genetic circuits have been developed to regulate behaviors of replicon RNA in responses to small molecules, which has broader applications, such as for quantitative expression of cargo genes, temporary expression of immunomodulatory cytokines or antigens for better cancer immunotherapy or vaccination, and for increased safety in use of self-replicating vectors or in combination with other viral-delivery vectors.

Example 2. In Vivo Expression from DD-nsP2 and nsP3-DD Genetic Circuits

Figure 5A:
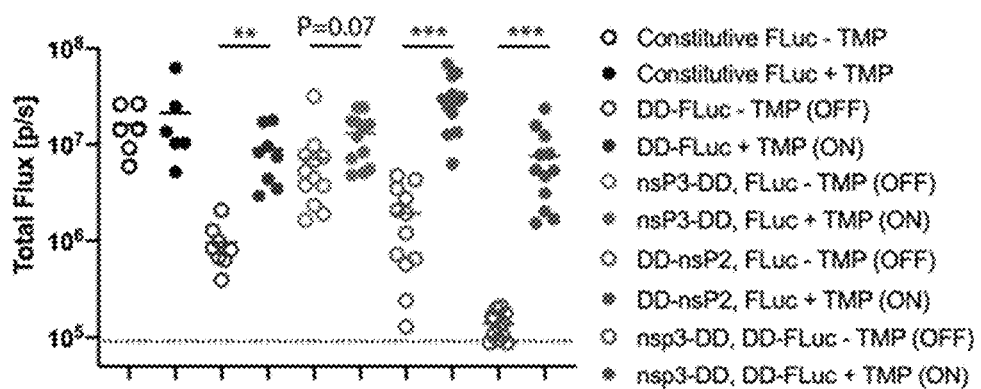
FIG. 5A-5B. In vivo gene expression from TMP-responsive replicons in muscles in BALB/c mice.
Figure 5B:
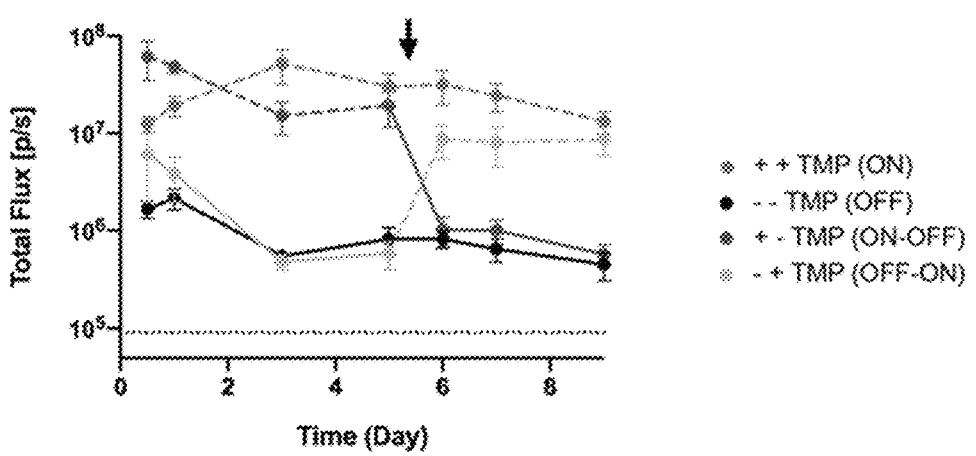

In vivo studies were conducted by intramuscular (i.m.) injection of replicons in BALB/c mice and demonstrated that fusing DD directly to the backbone of nsP2 or nsP3 genes successfully resulted in a regulatable in vivo "ON switch" circuit where the firefly luciferase (FLuc) payload was produced at a higher level in mice receiving TMP via diet at 0.2% w/w (+TMP, ON) compared with mice on standard rodent diet (−TMP, OFF). In addition, the replicon combining the nsP3-DD circuit with direct fusion of DD to payload (nsP3-DD, DD-FLuc) achieved the best regulation with ~100-fold difference between ON (+TMP) and OFF (−TMP) states (FIG. 5A). Furthermore, the regulation is reversible, such that the luciferase level remains low until TMP is added and returns to low levels when TMP is removed (FIG. 5B).

Figure 6:
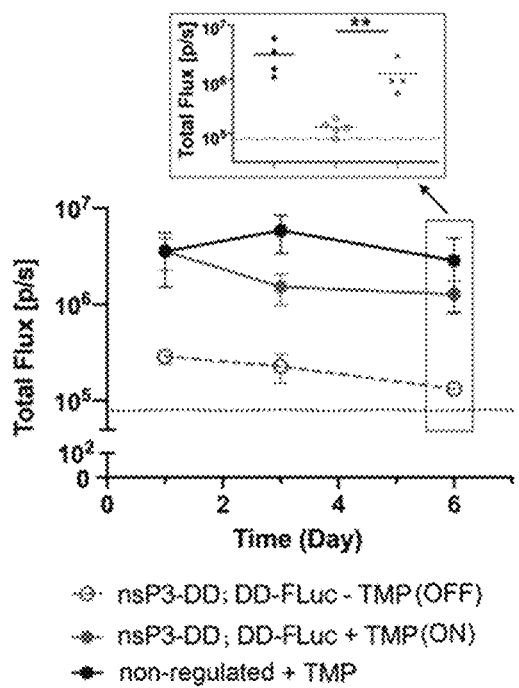
FIG. 6. In vivo gene expression from TMP-responsive replicons injected intratumorally in non-small cell lung cancer (NSCLC) KP tumor model. Replicons were injected intratumorally and electroporated at 100 V. The dotted line shows background levels of luminescence from untreated animals. Where indicated, TMP was provided in diet. Luminescence intensity from treated and untreated animals at 6 days post injection is indicated in the inset (n=4-5). From top to bottom at 6 days post injection, the following conditions are indicated: non-regulated+TMP; nsP3-DD, DD-FLuc+TMP (ON); nsP3-DD, DD-FLuc−TMP (OFF).

Next, the most promising candidate from the intramuscular studies, i.e., nsP3-DD, DD-FLuc circuit was tested intratumorally in B6 mice bearing non-small cell lung cancer (NSCLC) KP tumors. The nsP3-DD, DD-FLuc inducible replicon exhibited higher gene expression in tumors in the presence of TMP (10-fold higher FLuc bioluminescence) compared with that in the absence of TMP (FIG. 6).

Example 3. Cancer Cell Inhibition with nsP3-DD Genetic Circuits

Figure 7A:
FIG. 7A-7C. nsP3-DD, DD-gsdmD gene circuits.

The nsP3-DD circuit was also used for the regulated expression of the cell death effector molecule gasdermin D (gsdmD). Activated gasdermins are pore-forming proteins that insert in the cell membrane to induce cell death via pyroptosis. nsP3-DD gene circuits were designed containing two subgenomic promoters for the expression of secretory IL-12 fused to mouse serum albumin (IL12-MSA) and N-terminal pore-forming domain of gsdmD fused to DD (gsdmD-DD) (FIG. 7A). Following intratumoral injection and expression of IL-12 for several days, subsequent TMP-induced expression of gsdmD may therefore lead to immunogenic cell death and an optimized anti-tumor immune response.

This strategy requires that gsdmD expression is fully OFF prior to TMP administration, while IL-12 is continuously ON. Different nsP3-DD, DD-gsdmD genetic circuits were designed and synthesized for comparison. DD was appended to the N-terminus or C-terminus of gsdmD interspaced by one of 3 different linker sequences, either 1) a short flexible linker, 2) a long flexible linker, or 3) a rigid helical linker.

Figure 7B:
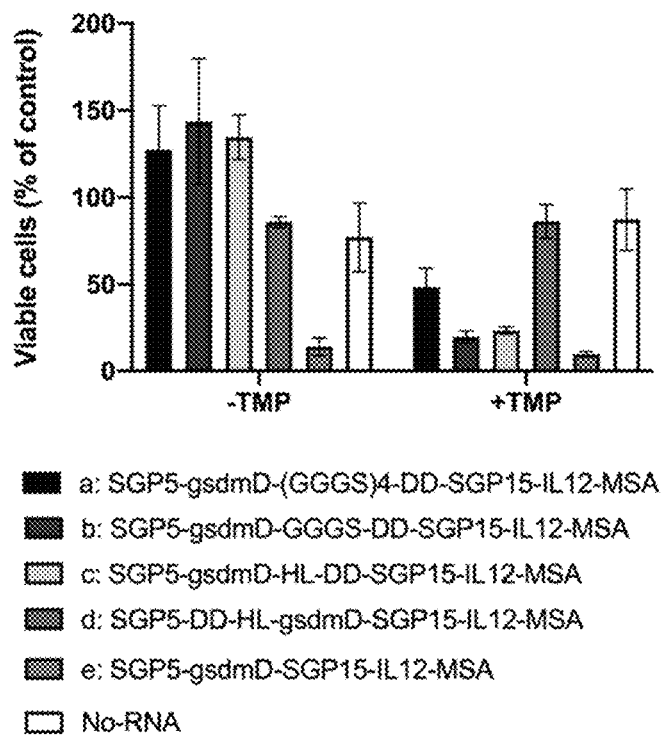
Figure 7C:
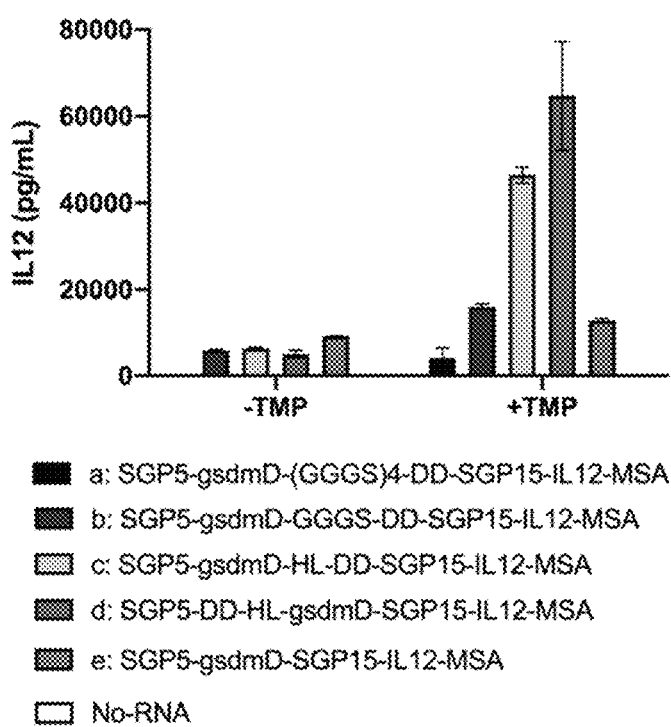

The genetic circuits were tested in vitro in non-small cell lung cancer (NSCLC) KP tumor cells. Replicons with DD fused to the C-terminus of gsdmD and with either a short or helical linker (construct b and c, respectively) resulted in switchable gsdmD expression in response to TMP (FIG. 7B). Presence of TMP resulted in higher gsdmD expression as indicated by the inhibition of cell viability that was measured by flow cytometry, whereas without TMP no inhibition of cell growth was observed. In addition, measurement of the expression level of secreted IL12-MSA in the supernatant of KP cells by ELISA showed that while the expression of IL12-MSA was higher in the presence of TMP, IL12-MSA expression remained ON even in the absence of TMP (FIG. 7C) providing a continuous source of IL12 which can attract immune cells into the tumor and help remodel the tumor microenvironment.

REFERENCES

1. Lundstrom, K. "Self-Replicating RNA Viruses for RNA Therapeutics". *Molecules* 23, 3310 (2018).

2. Vogel, A. B. et al. "Self-Amplifying RNA Vaccines Give Equivalent Protection against Influenza to mRNA Vaccines but at Much Lower Doses". *Mol. Ther.* 26, 446-455 (2018).
3. Lundstrom, K. "Replicon RNA Viral Vectors as Vaccines". *Vaccines* 4, 39 (2016).
4. Andries, O., Kitada, T., Bodner, K., Sanders, N. N. & Weiss, R. "Synthetic biology devices and circuits for RNA-based 'smart vaccines': a propositional review". *Expert Rev. Vaccines* 14, 313-331 (2015).
5. Zappasodi, R. & Merghoub, T. "Alphavirus-based vaccines in melanoma: Rationale and potential improvements in immunotherapeutic combinations". *Immunotherapy* vol. 7 981-997 (2015).
6. Bogers, W. M. et al. "Potent immune responses in rhesus macaques induced by nonviral delivery of a self-amplifying RNA vaccine expressing HIV type 1 envelope with a cationic nanoemulsion". *J. Infect. Dis.* 211, 947-955 (2015).
7. Granot, T., Yamanashi, Y. & Meruelo, D. "Sindbis viral vectors transiently deliver tumor-associated antigens to lymph nodes and elicit diversified antitumor CD8+ T-cell immunity". *Mol. Ther.* 22, 112-122 (2014).
8. Ljungberg, K. & Liljestrom, P. "Self-replicating alphavirus RNA vaccines". *Expert Rev. Vaccines* 14, 177-194 (2014).
9. Osada, T., Morse, M. A., Hobeika, A. & Lyerly Kim, H. "Novel recombinant alphaviral and adenoviral vectors for cancer immunotherapy". *Semin. Oncol.* 39, 305-310 (2012).
10. Pietilä, M. K., Hellstrom, K. & Ahola, T. "Alphavirus polymerase and RNA replication". *Virus Res.* 234, 44-57 (2017).
11. Rupp, J. C., Sokoloski, K. J., Gebhart, N. N. & Hardy, R. W. "Alphavirus RNA synthesis and non-structural protein functions". *J. Gen. Virol.* 96, 2483-2500 (2015).
12. Wroblewska, L. et al. "Mammalian synthetic circuits with RNA binding proteins delivered by RNA". *Nat. Biotechnol.* 33, 839-841 (2015).
13. Wagner, T. E. et al. "Small-molecule-based regulation of RNA-delivered circuits in mammalian cells". *Nat. Chem. Biol.* 14, 1043-1050 (2018).
14. Petrakova, O. et al. "Noncytopathic Replication of Venezuelan Equine Encephalitis Virus and Eastern Equine Encephalitis Virus Replicons in Mammalian Cells". *J. Virol.* 79, 7597-7608 (2005).
15. Li, Y. et al. "In vitro evolution of enhanced RNA replicons for immunotherapy". *Sci. Rep.* 9, 1-10 (2019).
16. Iwamoto, M., Bjorklund, T., Lundberg, C., Kirik, D. & Wandless, T. J. "A general chemical method to regulate protein stability in the mammalian central nervous system". *Chem Biol* 17, 981-988 (2010).
17. Miyazaki, Y., Imoto, H., Chen, L.-C. & Wandless, T. J. "Destabilizing Domains Derived from the Human Estrogen Receptor". *J. Am. Chem. Soc.* 134, 3942-3945 (2012).
18. Banaszynski, L. A., Chen, L., Maynard-Smith, L. A., Ooi, A. G. L. & Wandless, T. J. "A Rapid, Reversible, and Tunable Method to Regulate Protein Function in Living Cells Using Synthetic Small Molecules". *Cell* 126, 995-1004 (2006).

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided, URL addresses are provided as non-browser-executable codes, with periods of the respective web address in parentheses. The actual web addresses do not contain the parentheses.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

What is claimed is:

1. A genetic circuit for regulating responses of replicon RNA to small molecules, comprising one or more RNA replicons replicated by an RNA-dependent RNA polymerase (RdRp), wherein the one or more RNA replicons comprises one or more output sequences and a sequence encoding a nonstructural protein (nsP) 3 (nsP3) modified by fusion to a first destabilization domain (DD) which is stabilized in the presence of a first small molecule, wherein the genetic circuit is capable of being in an OFF state in the absence of the first small molecule or an ON state in the presence of the first-small molecule, wherein the ON state comprises an expression level of the one or more output sequences that is higher than the expression level of the one or more output sequences in the OFF state, and wherein transition from the OFF state to the ON state is faster than transition from the ON state to the OFF state.

2. The genetic circuit of claim 1, wherein the first DD is selected from an *E. coli* dihydrofolate reductase (DHFR)-derived destabilization domain (DDd), a human estrogen receptor ligand binding domain (DDe), or a FK506 binding protein (FKBP)-derived destabilization domain (DDf).

3. The genetic circuit of claim 1, wherein the first small molecule is selected from trimethoprim (TMP), 4-hydroxytamoxifen (4-OHT), or a Shield ligand.

4. The genetic circuit of claim 1, wherein the genetic circuit further comprises at least one of: a nsP2 modified by fusion to a second DD which is stabilized in the presence of a second small molecule, a nsP1 modified by fusion to a third DD which is stabilized in the presence of a third small molecule, or a nsP4 modified by fusion to a fourth DD which is stabilized in the presence of a fourth small molecule.

5. The genetic circuit of claim 4, wherein the second small molecule, the third small molecule, and the fourth small molecule are selected from trimethoprim (TMP), 4-hydroxytamoxifen (4-OHT), or a Shield ligand, or wherein the second DD, the third DD, and the fourth DD are selected from an *E. coli* dihydrofolate reductase (DHFR)-derived destabilization domain (DDd), a human estrogen receptor ligand binding domain (DDe), or a FK506 binding protein (FKBP)-derived destabilization domain (DDf).

6. The genetic circuit of claim 1, wherein the one or more RNA replicons are alphavirus-derived replicons.

7. The genetic circuit of claim 6, wherein the one or more replicons are replicated by an RNA-dependent RNA polymerase (RdRp), wherein the RdRp comprises nsP1, nsP2, nsP3, and nsP4.

8. The genetic circuit of claim 7, wherein the one or more output sequences are: i) operably linked to one or more promoters; ii) repressed by the expression of one or more effector sequences, wherein each effector sequence encodes a small molecule-regulatable RNA binding protein (RBP) and is operably linked to a promoter; or iii) are operably linked to the one or more promoters as set forth in i) and repressed by the one or more effector sequences as set forth in ii).

9. The genetic circuit of claim 8, wherein the one or more promoters of i) are a constitutive promoter or an inducible promoter or wherein the small molecule-regulatable RNA-binding protein (RBP) of ii) is modified by fusion to a small molecule-interacting domain.

10. The genetic circuit of claim 9, wherein the small molecule-interacting domain comprised by the small molecule-regulatable RBP is either a fifth DD which is stabilized in the presence of a fifth small molecule and expression of the one or more output sequences is derepressed in the presence of the fifth small molecule, wherein the fifth small molecule is selected from trimethoprim (TMP), 4-hydroxytamoxifen (4-OHT), Shield ligand, or doxycycline, or
wherein the small molecule-interacting domain comprised by the small molecule-regulatable RBP is a tetracycline repressor (TetR).

11. The genetic circuit of claim 9, wherein the expression of each effector sequence is constitutive or inducible, or wherein the one or more promoters of i), the one or more promoters of ii), or both is a subgenomic promoter.

12. The genetic circuit of claim 8, wherein the small molecule-regulatable RNA-binding protein (RBP) is L7Ae or DDX6, or
wherein the one or more output sequences encodes a protein, DNA, RNA, or miRNA.

13. The genetic circuit of claim 12, wherein the protein is an antigen that stimulates an immune response.

14. An isolated cell comprising the genetic circuit of claim 1.

15. A method of expressing one or more output sequences in a subject, comprising:
administering a composition comprising an effective amount of the genetic circuit of claim 1 to the subject; and
administering to the subject the first small molecule.

16. A method of expressing one or more output sequences in a subject, comprising:
administering a composition comprising an effective amount of the genetic circuit of claim 4 to the subject; and
administering to the subject at least one of the second small molecule, the third small molecule, or the fourth small molecule.

17. A method of expressing one or more output sequences in a subject, comprising:
administering a composition comprising an effective amount of the genetic circuit of claim 10 to the subject; and
administering to the subject the fifth small molecule or tetracycline.

18. The method of claim 16, wherein the first DD and the second DD are the same and the first small molecule and the second small molecule are the same, or
wherein the first DD and the second DD are different and the first small molecule and the second small molecule are different.

19. The method of claim 15, wherein each output sequence encodes a protein, DNA, RNA, or miRNA.

20. The method of claim 15, wherein the subject is a human.

* * * * *

SEQUENCE LISTING

```
<160> NUMBER OF SEQ ID NOS: 12

<210> SEQ ID NO 1
<211> LENGTH: 535
<212> TYPE: PRT
<213> ORGANISM: Venezuelan equine encephalitis virus

<400> SEQUENCE: 1

Met Glu Lys Val His Val Asp Ile Glu Glu Asp Ser Pro Phe Leu Arg
1               5                   10                  15

Ala Leu Gln Arg Ser Phe Pro Gln Phe Glu Val Glu Ala Lys Gln Val
            20                  25                  30

Thr Asp Asn Asp His Ala Asn Ala Arg Ala Phe Ser His Leu Ala Ser
        35                  40                  45

Lys Leu Ile Glu Thr Glu Val Asp Pro Ser Asp Thr Ile Leu Asp Ile
    50                  55                  60

Gly Ser Ala Pro Ala Arg Arg Met Tyr Ser Lys His Lys Tyr His Cys
65                  70                  75                  80

Ile Cys Pro Met Arg Cys Ala Glu Asp Pro Asp Arg Leu Tyr Lys Tyr
                85                  90                  95

Ala Thr Lys Leu Lys Lys Asn Cys Lys Glu Ile Thr Asp Lys Glu Leu
            100                 105                 110

Asp Lys Lys Met Lys Glu Leu Ala Ala Val Met Ser Asp Pro Asp Leu
        115                 120                 125

Glu Thr Glu Thr Met Cys Leu His Asp Asp Glu Ser Cys Arg Tyr Glu
    130                 135                 140

Gly Gln Val Ala Val Tyr Gln Asp Val Tyr Ala Val Asp Gly Pro Thr
145                 150                 155                 160

Ser Leu Tyr His Gln Ala Asn Lys Gly Val Arg Val Ala Tyr Trp Ile
                165                 170                 175

Gly Phe Asp Thr Thr Pro Phe Met Phe Lys Asn Leu Ala Gly Ala Tyr
            180                 185                 190

Pro Ser Tyr Ser Thr Asn Trp Ala Asp Glu Thr Val Leu Thr Ala Arg
        195                 200                 205

Asn Ile Gly Leu Cys Ser Ser Asp Val Met Glu Arg Ser Arg Arg Gly
    210                 215                 220

Met Ser Ile Leu Arg Lys Lys Tyr Leu Lys Pro Ser Asn Asn Val Leu
225                 230                 235                 240

Phe Ser Val Gly Ser Thr Ile Tyr His Glu Lys Arg Asp Leu Leu Arg
                245                 250                 255

Ser Trp His Leu Pro Ser Val Phe His Leu Arg Gly Lys Gln Asn Tyr
            260                 265                 270

Thr Cys Arg Cys Glu Thr Ile Val Ser Cys Asp Gly Tyr Val Val Lys
        275                 280                 285

Arg Ile Ala Ile Ser Pro Gly Leu Tyr Gly Lys Pro Ser Gly Tyr Ala
    290                 295                 300

Ala Thr Met His Arg Glu Gly Phe Leu Cys Cys Lys Val Thr Asp Thr
```

-continued

```
              305                 310                 315                 320

Leu Asn Gly Glu Arg Val Ser Phe Pro Val Cys Thr Tyr Val Pro Ala
                        325                 330                 335

Thr Leu Cys Asp Gln Met Thr Gly Ile Leu Ala Thr Asp Val Ser Ala
                        340                 345                 350

Asp Asp Ala Gln Lys Leu Leu Val Gly Leu Asn Gln Arg Ile Val Val
                        355                 360                 365

Asn Gly Arg Thr Gln Arg Asn Thr Asn Thr Met Lys Asn Tyr Leu Leu
                        370                 375                 380

Pro Val Val Ala Gln Ala Phe Ala Arg Trp Ala Lys Glu Tyr Lys Glu
        385                 390                 395                 400

Asp Gln Glu Asp Glu Arg Pro Leu Gly Leu Arg Asp Arg Gln Leu Val
                        405                 410                 415

Met Gly Cys Cys Trp Ala Phe Arg Arg His Lys Ile Thr Ser Ile Tyr
                        420                 425                 430

Lys Arg Pro Asp Thr Gln Thr Ile Ile Lys Val Asn Ser Asp Phe His
                        435                 440                 445

Ser Phe Val Leu Pro Arg Ile Gly Ser Asn Thr Leu Glu Ile Gly Leu
                        450                 455                 460

Arg Thr Arg Ile Arg Lys Met Leu Glu Glu His Lys Glu Pro Ser Pro
        465                 470                 475                 480

Leu Ile Thr Ala Glu Asp Ile Gln Glu Ala Lys Cys Ala Ala Asp Glu
                        485                 490                 495

Ala Lys Glu Val Arg Glu Ala Glu Glu Leu Arg Ala Ala Leu Pro Pro
                        500                 505                 510

Leu Ala Ala Asp Phe Glu Glu Pro Thr Leu Glu Ala Asp Val Asp Leu
                        515                 520                 525

Met Leu Gln Glu Ala Gly Ala
                        530                 535

<210> SEQ ID NO 2
<211> LENGTH: 794
<212> TYPE: PRT
<213> ORGANISM: Venezuelan equine encephalitis virus

<400> SEQUENCE: 2

Gly Ser Val Glu Thr Pro Arg Gly Leu Ile Lys Val Thr Ser Tyr Ala
        1               5                   10                  15

Gly Glu Asp Lys Ile Gly Ser Tyr Ala Val Leu Ser Pro Gln Ala Val
                        20                  25                  30

Leu Lys Ser Glu Lys Leu Ser Cys Ile His Pro Leu Ala Glu Gln Val
                        35                  40                  45

Ile Val Ile Thr His Ser Gly Arg Lys Gly Arg Tyr Ala Val Glu Pro
                50                  55                  60

Tyr His Gly Lys Val Val Val Pro Glu Gly His Ala Ile Pro Val Gln
        65                  70                  75                  80

Asp Phe Gln Ala Leu Ser Glu Ser Ala Thr Ile Val Tyr Asn Glu Arg
                        85                  90                  95

Glu Phe Val Asn Arg Tyr Leu His His Ile Ala Thr His Gly Gly Ala
                        100                 105                 110

Leu Asn Thr Asp Glu Glu Tyr Tyr Lys Thr Val Lys Pro Ser Glu His
                        115                 120                 125

Asp Gly Glu Tyr Leu Tyr Asp Ile Asp Arg Lys Gln Cys Val Lys Lys
                130                 135                 140
```

```
Glu Leu Val Thr Gly Leu Gly Leu Thr Gly Glu Leu Val Asp Pro Pro
145                 150                 155                 160

Phe His Glu Phe Ala Tyr Glu Ser Leu Arg Thr Arg Pro Ala Ala Pro
            165                 170                 175

Tyr Gln Val Pro Thr Ile Gly Val Tyr Gly Val Pro Gly Ser Gly Lys
            180                 185                 190

Ser Gly Ile Ile Lys Ser Ala Val Thr Lys Asp Leu Val Val Ser
        195                 200                 205

Ala Lys Lys Glu Asn Cys Ala Glu Ile Ile Arg Asp Val Lys Lys Met
    210                 215                 220

Lys Gly Leu Asp Val Asn Ala Arg Thr Val Asp Ser Val Leu Leu Asn
225                 230                 235                 240

Gly Cys Lys His Pro Val Glu Thr Leu Tyr Ile Asp Glu Ala Phe Ala
                245                 250                 255

Cys His Ala Gly Thr Leu Arg Ala Leu Ile Ala Ile Arg Pro Lys
            260                 265                 270

Lys Ala Val Leu Cys Gly Asp Pro Lys Gln Cys Gly Phe Phe Asn Met
        275                 280                 285

Met Cys Leu Lys Val His Phe Asn His Glu Ile Cys Thr Gln Val Phe
290                 295                 300

His Lys Ser Ile Ser Arg Arg Cys Thr Lys Ser Val Thr Ser Val Val
305                 310                 315                 320

Ser Thr Leu Phe Tyr Asp Lys Arg Met Arg Thr Thr Asn Pro Lys Glu
            325                 330                 335

Thr Lys Ile Val Ile Asp Thr Thr Gly Ser Thr Lys Pro Lys Gln Asp
            340                 345                 350

Asp Leu Ile Leu Thr Cys Phe Arg Gly Trp Val Lys Gln Leu Gln Ile
            355                 360                 365

Asp Tyr Lys Gly Asn Glu Ile Met Thr Ala Ala Ser Gln Gly Leu
        370                 375                 380

Thr Arg Lys Gly Val Tyr Ala Val Arg Tyr Lys Val Asn Glu Asn Pro
385                 390                 395                 400

Leu Tyr Ala Pro Thr Ser Glu His Val Asn Val Leu Leu Thr Arg Thr
            405                 410                 415

Glu Asp Arg Ile Val Trp Lys Thr Leu Ala Gly Asp Pro Trp Ile Lys
            420                 425                 430

Ile Leu Thr Ala Lys Tyr Pro Gly Asn Phe Thr Ala Thr Ile Glu Glu
            435                 440                 445

Trp Gln Ala Glu His Asp Ala Ile Met Arg His Ile Leu Glu Arg Pro
450                 455                 460

Asp Pro Thr Asp Val Phe Gln Asn Lys Ala Asn Val Cys Trp Ala Lys
465                 470                 475                 480

Ala Leu Val Pro Val Leu Lys Thr Ala Gly Ile Asp Met Thr Thr Glu
            485                 490                 495

Gln Trp Asn Thr Val Asp Tyr Phe Glu Thr Asp Lys Ala His Ser Ala
            500                 505                 510

Glu Ile Val Leu Asn Gln Leu Cys Val Arg Phe Phe Gly Leu Asp Leu
            515                 520                 525

Asp Ser Gly Leu Phe Ser Ala Pro Thr Val Pro Leu Ser Ile Arg Asn
            530                 535                 540

Asn His Trp Asp Asn Ser Pro Ser Pro Asn Met Tyr Gly Leu Asn Lys
545                 550                 555                 560

Glu Val Val Arg Gln Leu Ser Arg Arg Tyr Pro Gln Leu Pro Arg Ala
```

```
                    565                 570                 575
Val Ala Thr Gly Arg Val Tyr Asp Met Asn Thr Gly Thr Leu Arg Asn
                580                 585                 590

Tyr Asp Pro Arg Ile Asn Leu Val Pro Val Asn Arg Arg Leu Pro His
            595                 600             605

Ala Leu Val Leu His His Asn Glu His Pro Gln Ser Asp Phe Ser Ser
        610                 615                 620

Phe Val Ser Lys Leu Lys Gly Arg Thr Val Leu Val Val Gly Glu Lys
625                 630                 635                 640

Leu Ser Val Pro Gly Lys Lys Val Asp Trp Leu Ser Asp Gln Pro Glu
                645                 650                 655

Ala Thr Phe Arg Ala Arg Leu Asp Leu Gly Ile Pro Gly Asp Val Pro
            660                 665                 670

Lys Tyr Asp Ile Val Phe Ile Asn Val Arg Thr Pro Tyr Lys Tyr His
        675                 680                 685

His Tyr Gln Gln Cys Glu Asp His Ala Ile Lys Leu Ser Met Leu Thr
    690                 695                 700

Lys Lys Ala Cys Leu His Leu Asn Pro Gly Gly Thr Cys Val Ser Ile
705                 710                 715                 720

Gly Tyr Gly Tyr Ala Asp Arg Ala Ser Glu Ser Ile Ile Gly Ala Ile
                725                 730                 735

Ala Arg Gln Phe Lys Phe Ser Arg Val Cys Lys Pro Lys Ser Ser His
            740                 745                 750

Glu Glu Thr Glu Val Leu Phe Val Phe Ile Gly Tyr Asp Arg Lys Ala
        755                 760                 765

Arg Thr His Asn Pro Tyr Lys Leu Ser Ser Thr Leu Thr Asn Ile Tyr
    770                 775                 780

Thr Gly Ser Arg Leu His Glu Ala Gly Cys
785                 790

<210> SEQ ID NO 3
<211> LENGTH: 557
<212> TYPE: PRT
<213> ORGANISM: Venezuelan equine encephalitis virus

<400> SEQUENCE: 3

Ala Pro Ser Tyr His Val Val Arg Gly Asp Ile Ala Thr Ala Thr Glu
1               5                   10                  15

Gly Val Ile Ile Asn Ala Ala Asn Ser Lys Gly Gln Pro Gly Gly Gly
            20                  25                  30

Val Cys Gly Ala Leu Tyr Lys Lys Phe Pro Glu Ser Phe Asp Leu Gln
        35                  40                  45

Pro Ile Glu Val Gly Lys Ala Arg Leu Val Lys Gly Ala Ala Lys His
    50                  55                  60

Ile Ile His Ala Val Gly Pro Asn Phe Asn Lys Val Ser Glu Val Glu
65                  70                  75                  80

Gly Asp Lys Gln Leu Ala Glu Ala Tyr Glu Ser Ile Ala Lys Ile Val
                85                  90                  95

Asn Asp Asn Asn Tyr Lys Ser Val Ala Ile Pro Leu Leu Ser Thr Gly
            100                 105                 110

Ile Phe Ser Gly Asn Lys Asp Arg Leu Thr Gln Ser Leu Asn His Leu
        115                 120                 125

Leu Thr Ala Leu Asp Thr Thr Asp Ala Asp Val Ala Ile Tyr Cys Arg
    130                 135                 140
```

```
Asp Lys Lys Trp Glu Met Thr Leu Lys Glu Ala Val Ala Arg Arg Glu
145                 150                 155                 160

Ala Val Glu Glu Ile Cys Ile Ser Asp Ser Ser Val Thr Glu Pro
            165                 170                 175

Asp Ala Glu Leu Val Arg Val His Pro Lys Ser Ser Leu Ala Gly Arg
                180                 185                 190

Lys Gly Tyr Ser Thr Ser Asp Gly Lys Thr Phe Ser Tyr Leu Glu Gly
            195                 200                 205

Thr Lys Phe His Gln Ala Ala Lys Asp Ile Ala Glu Ile Asn Ala Met
    210                 215                 220

Trp Pro Val Ala Thr Glu Ala Asn Glu Gln Val Cys Met Tyr Ile Leu
225                 230                 235                 240

Gly Glu Ser Met Ser Ser Ile Arg Ser Lys Cys Pro Val Glu Glu Ser
                245                 250                 255

Glu Ala Ser Thr Pro Pro Ser Thr Leu Pro Cys Leu Cys Ile His Ala
            260                 265                 270

Met Thr Pro Glu Arg Val Gln Arg Leu Lys Ala Ser Arg Pro Glu Gln
        275                 280                 285

Ile Thr Val Cys Ser Ser Phe Pro Leu Pro Lys Tyr Arg Ile Thr Gly
    290                 295                 300

Val Gln Lys Ile Gln Cys Ser Gln Pro Ile Leu Phe Ser Pro Lys Val
305                 310                 315                 320

Pro Ala Tyr Ile His Pro Arg Lys Tyr Leu Val Glu Thr Pro Pro Val
                325                 330                 335

Glu Glu Thr Pro Glu Ser Pro Ala Glu Asn Gln Ser Thr Glu Gly Thr
            340                 345                 350

Pro Glu Gln Pro Ala Leu Val Asn Val Asp Ala Thr Arg Thr Arg Met
        355                 360                 365

Pro Glu Pro Ile Ile Ile Glu Glu Glu Glu Asp Ser Ile Ser Leu
370                 375                 380

Leu Ser Asp Gly Pro Thr His Gln Val Leu Gln Val Glu Ala Asp Ile
385                 390                 395                 400

His Gly Ser Pro Ser Val Ser Ser Ser Ser Trp Ser Ile Pro His Ala
                405                 410                 415

Ser Asp Phe Asp Val Asp Ser Leu Ser Ile Leu Asp Thr Leu Asp Gly
            420                 425                 430

Ala Ser Val Thr Ser Gly Ala Val Ser Ala Glu Thr Asn Ser Tyr Phe
        435                 440                 445

Ala Arg Ser Met Glu Phe Arg Ala Arg Pro Val Pro Ala Pro Arg Thr
450                 455                 460

Val Phe Arg Asn Pro His Pro Ala Pro Arg Thr Arg Thr Pro Pro
465                 470                 475                 480

Leu Ala His Ser Arg Ala Ser Ser Arg Thr Ser Leu Val Ser Thr Pro
                485                 490                 495

Pro Gly Val Asn Arg Val Ile Thr Arg Glu Glu Leu Glu Ala Leu Thr
            500                 505                 510

Pro Ser Arg Ala Pro Ser Arg Ser Ala Ser Arg Thr Ser Leu Val Ser
        515                 520                 525

Asn Pro Pro Gly Val Asn Arg Val Ile Thr Arg Glu Glu Phe Glu Ala
            530                 535                 540

Phe Val Ala Gln Gln Gln Arg Arg Phe Asp Ala Gly Ala
545                 550                 555
```

```
<210> SEQ ID NO 4
<211> LENGTH: 606
<212> TYPE: PRT
<213> ORGANISM: Venezuelan equine encephalitis virus

<400> SEQUENCE: 4

Tyr Ile Phe Ser Ser Asp Thr Gly Gln Gly His Leu Gln Gln Lys Ser
1               5                   10                  15

Val Arg Gln Thr Val Leu Ser Glu Val Val Leu Glu Arg Thr Glu Leu
            20                  25                  30

Glu Ile Ser Tyr Ala Pro Arg Leu Asp Gln Glu Lys Glu Glu Leu Leu
        35                  40                  45

Arg Lys Lys Leu Gln Leu Asn Pro Thr Pro Ala Asn Arg Ser Arg Tyr
    50                  55                  60

Gln Ser Arg Arg Val Glu Asn Met Lys Ala Ile Thr Ala Arg Arg Ile
65                  70                  75                  80

Leu Gln Gly Leu Gly His Tyr Leu Lys Ala Glu Gly Lys Val Glu Cys
                85                  90                  95

Tyr Arg Thr Leu His Pro Val Pro Leu Tyr Ser Ser Ser Val Asn Arg
            100                 105                 110

Ala Phe Ser Ser Pro Lys Val Ala Val Glu Ala Cys Asn Ala Met Leu
        115                 120                 125

Lys Glu Asn Phe Pro Thr Val Ala Ser Tyr Cys Ile Ile Pro Glu Tyr
    130                 135                 140

Asp Ala Tyr Leu Asp Met Val Asp Gly Ala Ser Cys Cys Leu Asp Thr
145                 150                 155                 160

Ala Ser Phe Cys Pro Ala Lys Leu Arg Ser Phe Pro Lys Lys His Ser
                165                 170                 175

Tyr Leu Glu Pro Thr Ile Arg Ser Ala Val Pro Ser Ala Ile Gln Asn
            180                 185                 190

Thr Leu Gln Asn Val Leu Ala Ala Ala Thr Lys Arg Asn Cys Asn Val
        195                 200                 205

Thr Gln Met Arg Glu Leu Pro Val Leu Asp Ser Ala Ala Phe Asn Val
    210                 215                 220

Glu Cys Phe Lys Lys Tyr Ala Cys Asn Asn Glu Tyr Trp Glu Thr Phe
225                 230                 235                 240

Lys Glu Asn Pro Ile Arg Leu Thr Glu Glu Asn Val Val Asn Tyr Ile
                245                 250                 255

Thr Lys Leu Lys Gly Pro Lys Ala Ala Ala Leu Phe Ala Lys Thr His
            260                 265                 270

Asn Leu Asn Met Leu Gln Asp Ile Pro Met Asp Arg Phe Val Met Asp
        275                 280                 285

Leu Lys Arg Asp Val Lys Val Thr Pro Gly Thr Lys His Thr Glu Glu
    290                 295                 300

Arg Pro Lys Val Gln Val Ile Gln Ala Ala Asp Pro Leu Ala Thr Ala
305                 310                 315                 320

Asp Leu Cys Gly Ile His Arg Glu Leu Val Arg Arg Leu Asn Ala Val
                325                 330                 335

Leu Leu Pro Asn Ile His Thr Leu Phe Asp Met Ser Ala Glu Asp Phe
            340                 345                 350

Asp Ala Ile Ile Ala Glu His Phe Gln Pro Gly Asp Cys Val Leu Glu
        355                 360                 365

Thr Asp Ile Ala Ser Phe Asp Lys Ser Glu Asp Asp Ala Met Ala Leu
    370                 375                 380
```

```
Thr Ala Leu Met Ile Leu Glu Asp Leu Gly Val Asp Ala Glu Leu Leu
385                 390                 395                 400

Thr Leu Ile Glu Ala Ala Phe Gly Glu Ile Ser Ser Ile His Leu Pro
                405                 410                 415

Thr Lys Thr Lys Phe Lys Phe Gly Ala Met Met Lys Ser Gly Met Phe
            420                 425                 430

Leu Thr Leu Phe Val Asn Thr Val Ile Asn Ile Val Ile Ala Ser Arg
        435                 440                 445

Val Leu Arg Glu Arg Leu Thr Gly Ser Pro Cys Ala Ala Phe Ile Gly
    450                 455                 460

Asp Asp Asn Ile Val Lys Gly Val Lys Ser Asp Lys Leu Met Ala Asp
465                 470                 475                 480

Arg Cys Ala Thr Trp Leu Asn Met Glu Val Lys Ile Ile Asp Ala Val
                485                 490                 495

Val Gly Glu Lys Ala Pro Tyr Phe Cys Gly Gly Phe Ile Leu Cys Asp
            500                 505                 510

Ser Val Thr Gly Thr Ala Cys Arg Val Ala Asp Pro Leu Lys Arg Leu
        515                 520                 525

Phe Lys Leu Gly Lys Pro Leu Ala Val Asp Asp Glu His Asp Asp Asp
    530                 535                 540

Arg Arg Arg Ala Leu His Glu Glu Ser Thr Arg Trp Asn Arg Val Gly
545                 550                 555                 560

Ile Leu Pro Glu Leu Cys Lys Ala Val Glu Ser Arg Tyr Glu Thr Val
                565                 570                 575

Gly Thr Ser Ile Ile Val Met Ala Met Thr Thr Leu Ala Ser Ser Val
            580                 585                 590

Lys Ser Phe Ser Tyr Leu Arg Gly Ala Pro Ile Thr Leu Tyr
        595                 600                 605

<210> SEQ ID NO 5
<211> LENGTH: 540
<212> TYPE: PRT
<213> ORGANISM: Sindbis virus

<400> SEQUENCE: 5

Met Glu Lys Pro Val Val Asn Val Asp Val Asp Pro Gln Ser Pro Phe
1               5                   10                  15

Val Val Gln Leu Gln Lys Ser Phe Pro Gln Phe Glu Val Val Ala Gln
            20                  25                  30

Gln Val Thr Pro Asn Asp His Ala Asn Ala Arg Ala Phe Ser His Leu
        35                  40                  45

Ala Ser Lys Leu Ile Glu Leu Glu Val Pro Thr Thr Ala Thr Ile Leu
    50                  55                  60

Asp Ile Gly Ser Ala Pro Ala Arg Arg Met Phe Ser Glu His Gln Tyr
65                  70                  75                  80

His Cys Val Cys Pro Met Arg Ser Pro Glu Asp Pro Asp Arg Met Met
                85                  90                  95

Lys Tyr Ala Ser Lys Leu Ala Glu Lys Ala Cys Lys Ile Thr Asn Lys
            100                 105                 110

Asn Leu His Glu Lys Ile Lys Asp Leu Arg Thr Val Leu Asp Thr Pro
        115                 120                 125

Asp Ala Glu Thr Pro Ser Leu Cys Phe His Asn Asp Val Thr Cys Asn
    130                 135                 140

Met Arg Ala Glu Tyr Ser Val Met Gln Asp Val Tyr Ile Asn Ala Pro
145                 150                 155                 160
```

-continued

```
Gly Thr Ile Tyr His Gln Ala Met Lys Gly Val Arg Thr Leu Tyr Trp
                165                 170                 175
Ile Gly Phe Asp Thr Thr Gln Phe Met Phe Ser Ala Met Ala Gly Ser
            180                 185                 190
Tyr Pro Ala Tyr Asn Thr Asn Trp Ala Asp Glu Lys Val Leu Glu Ala
        195                 200                 205
Arg Asn Ile Gly Leu Cys Ser Thr Lys Leu Ser Glu Gly Arg Thr Gly
    210                 215                 220
Lys Leu Ser Ile Met Arg Lys Lys Glu Leu Lys Pro Gly Ser Arg Val
225                 230                 235                 240
Tyr Phe Ser Val Gly Ser Thr Leu Tyr Pro Glu His Arg Ala Ser Leu
                245                 250                 255
Gln Ser Trp His Leu Pro Ser Val Phe His Leu Asn Gly Lys Gln Ser
            260                 265                 270
Tyr Thr Cys Arg Cys Asp Thr Val Val Ser Cys Glu Gly Tyr Val Val
        275                 280                 285
Lys Lys Ile Thr Ile Ser Pro Gly Ile Thr Gly Glu Thr Val Gly Tyr
    290                 295                 300
Ala Val Thr His Asn Ser Glu Gly Phe Leu Leu Cys Lys Val Thr Asp
305                 310                 315                 320
Thr Val Lys Gly Glu Arg Val Ser Phe Pro Val Cys Thr Tyr Ile Pro
                325                 330                 335
Ala Thr Ile Cys Asp Gln Met Thr Gly Ile Met Ala Thr Asp Ile Ser
            340                 345                 350
Pro Asp Asp Ala Gln Lys Leu Leu Val Gly Leu Asn Gln Arg Ile Val
        355                 360                 365
Ile Asn Gly Arg Thr Asn Arg Asn Thr Asn Thr Met Gln Asn Tyr Leu
    370                 375                 380
Leu Pro Ile Ile Ala Gln Gly Phe Ser Lys Trp Ala Lys Glu Arg Lys
385                 390                 395                 400
Asp Asp Leu Asp Asn Glu Lys Met Leu Gly Thr Arg Glu Arg Lys Leu
                405                 410                 415
Thr Tyr Gly Cys Leu Trp Ala Phe Arg Thr Lys Lys Val His Ser Phe
            420                 425                 430
Tyr Arg Pro Pro Gly Thr Gln Thr Cys Val Lys Val Pro Ala Ser Phe
        435                 440                 445
Ser Ala Phe Pro Met Ser Ser Val Trp Thr Thr Ser Leu Pro Met Ser
450                 455                 460
Leu Arg Gln Lys Leu Lys Leu Ala Leu Gln Pro Lys Lys Glu Glu Lys
465                 470                 475                 480
Leu Leu Gln Val Ser Glu Glu Leu Val Met Glu Ala Lys Ala Ala Phe
                485                 490                 495
Glu Asp Ala Gln Glu Glu Ala Arg Ala Glu Lys Leu Arg Glu Ala Leu
            500                 505                 510
Pro Pro Leu Val Ala Asp Lys Gly Ile Glu Ala Ala Glu Val Val
        515                 520                 525
Cys Glu Val Glu Gly Leu Gln Ala Asp Ile Gly Ala
    530                 535                 540

<210> SEQ ID NO 6
<211> LENGTH: 807
<212> TYPE: PRT
<213> ORGANISM: Sindbis virus
```

<400> SEQUENCE: 6

```
Ala Leu Val Glu Thr Pro Arg Gly His Val Arg Ile Ile Pro Gln Ala
1               5                   10                  15

Asn Asp Arg Met Ile Gly Gln Tyr Ile Val Val Ser Pro Asn Ser Val
            20                  25                  30

Leu Lys Asn Ala Lys Leu Ala Pro Ala His Pro Leu Ala Asp Gln Val
        35                  40                  45

Lys Ile Ile Thr His Ser Gly Arg Ser Gly Arg Tyr Ala Val Glu Pro
    50                  55                  60

Tyr Asp Ala Lys Val Leu Met Pro Ala Gly Gly Ala Val Pro Trp Pro
65                  70                  75                  80

Glu Phe Leu Ala Leu Ser Glu Ser Ala Thr Leu Val Tyr Asn Glu Arg
                85                  90                  95

Glu Phe Val Asn Arg Lys Leu Tyr His Ile Ala Met His Gly Pro Ala
            100                 105                 110

Lys Asn Thr Glu Glu Glu Gln Tyr Lys Val Thr Lys Ala Glu Leu Ala
        115                 120                 125

Glu Thr Glu Tyr Val Phe Asp Val Asp Lys Lys Arg Cys Val Lys Lys
    130                 135                 140

Glu Glu Ala Ser Gly Leu Val Leu Ser Gly Glu Leu Thr Asn Pro Pro
145                 150                 155                 160

Tyr His Glu Leu Ala Leu Glu Gly Leu Lys Thr Arg Pro Ala Val Pro
                165                 170                 175

Tyr Lys Val Glu Thr Ile Gly Val Ile Gly Thr Pro Gly Ser Gly Lys
            180                 185                 190

Ser Ala Ile Ile Lys Ser Thr Val Thr Ala Arg Asp Leu Val Thr Ser
        195                 200                 205

Gly Lys Lys Glu Asn Cys Arg Glu Ile Glu Ala Asp Val Leu Arg Leu
    210                 215                 220

Arg Gly Met Gln Ile Thr Ser Lys Thr Val Asp Ser Val Met Leu Asn
225                 230                 235                 240

Gly Cys His Lys Ala Val Glu Val Leu Tyr Val Asp Glu Ala Phe Ala
                245                 250                 255

Cys His Ala Gly Ala Leu Leu Ala Leu Ile Ala Ile Val Arg Pro Arg
            260                 265                 270

Lys Lys Val Val Leu Cys Gly Asp Pro Met Gln Cys Gly Phe Phe Asn
        275                 280                 285

Met Met Gln Leu Lys Val His Phe Asn His Pro Glu Lys Asp Ile Cys
    290                 295                 300

Thr Lys Thr Phe Tyr Lys Tyr Ile Ser Arg Arg Cys Thr Gln Pro Val
305                 310                 315                 320

Thr Ala Ile Val Ser Thr Leu His Tyr Asp Gly Lys Met Lys Thr Thr
                325                 330                 335

Asn Pro Cys Lys Lys Asn Ile Glu Ile Asp Ile Thr Gly Ala Thr Lys
            340                 345                 350

Pro Lys Pro Gly Asp Ile Ile Leu Thr Cys Phe Arg Gly Trp Val Lys
        355                 360                 365

Gln Leu Gln Ile Asp Tyr Pro Gly His Glu Val Met Thr Ala Ala Ala
    370                 375                 380

Ser Gln Gly Leu Thr Arg Lys Gly Val Tyr Ala Val Arg Gln Lys Val
385                 390                 395                 400

Asn Glu Asn Pro Leu Tyr Ala Ile Thr Ser Glu His Val Asn Val Leu
                405                 410                 415
```

-continued

Leu Thr Arg Thr Glu Asp Arg Leu Val Trp Lys Thr Leu Gln Gly Asp
            420                 425                 430

Pro Trp Ile Lys Gln Pro Thr Asn Ile Pro Lys Gly Asn Phe Gln Ala
            435                 440                 445

Thr Ile Glu Asp Trp Glu Ala Glu His Lys Gly Ile Ile Ala Ala Ile
450                 455                 460

Asn Ser Pro Thr Pro Arg Ala Asn Pro Phe Ser Cys Lys Thr Asn Val
465                 470                 475                 480

Cys Trp Ala Lys Ala Leu Glu Pro Ile Leu Ala Thr Ala Gly Ile Val
                485                 490                 495

Leu Thr Gly Cys Gln Trp Ser Glu Leu Phe Pro Gln Phe Ala Asp Asp
                500                 505                 510

Lys Pro His Ser Ala Ile Tyr Ala Leu Asp Val Ile Cys Ile Lys Phe
            515                 520                 525

Phe Gly Met Asp Leu Thr Ser Gly Leu Phe Ser Lys Gln Ser Ile Pro
530                 535                 540

Leu Thr Tyr His Pro Ala Asp Ser Ala Arg Pro Val Ala His Trp Asp
545                 550                 555                 560

Asn Ser Pro Gly Thr Arg Lys Tyr Gly Tyr Asp His Ala Ile Ala Ala
                565                 570                 575

Glu Leu Ser Arg Arg Phe Pro Val Phe Gln Leu Ala Gly Lys Gly Thr
            580                 585                 590

Gln Leu Asp Leu Gln Thr Gly Arg Thr Arg Val Ile Ser Ala Gln His
            595                 600                 605

Asn Leu Val Pro Val Asn Arg Asn Leu Pro His Ala Leu Val Pro Glu
610                 615                 620

Tyr Lys Glu Lys Gln Pro Gly Pro Val Lys Lys Phe Leu Asn Gln Phe
625                 630                 635                 640

Lys His His Ser Val Leu Val Ser Glu Glu Lys Ile Glu Ala Pro
                645                 650                 655

Arg Lys Arg Ile Glu Trp Ile Ala Pro Ile Gly Ile Ala Gly Ala Asp
                660                 665                 670

Lys Asn Tyr Asn Leu Ala Phe Gly Phe Pro Pro Gln Ala Arg Tyr Asp
            675                 680                 685

Leu Val Phe Ile Asn Ile Gly Thr Lys Tyr Arg Asn His His Phe Gln
690                 695                 700

Gln Cys Glu Asp His Ala Ala Thr Leu Lys Thr Leu Ser Arg Ser Ala
705                 710                 715                 720

Leu Asn Cys Leu Asn Pro Gly Gly Thr Leu Val Lys Ser Tyr Gly
                725                 730                 735

Tyr Ala Asp Arg Asn Ser Glu Asp Val Val Thr Ala Leu Ala Arg Lys
            740                 745                 750

Phe Val Arg Val Ser Ala Ala Arg Pro Asp Cys Val Ser Ser Asn Thr
            755                 760                 765

Glu Met Tyr Leu Ile Phe Arg Gln Leu Asp Asn Ser Arg Thr Arg Gln
            770                 775                 780

Phe Thr Pro His His Leu Asn Cys Val Ile Ser Ser Val Tyr Glu Gly
785                 790                 795                 800

Thr Arg Asp Gly Val Gly Ala
                805

<210> SEQ ID NO 7
<211> LENGTH: 549

-continued

<212> TYPE: PRT
<213> ORGANISM: Sindbis virus

<400> SEQUENCE: 7

```
Ala Pro Ser Tyr Arg Thr Lys Arg Glu Asn Ile Ala Asp Cys Gln Glu
1               5                   10                  15

Glu Ala Val Val Asn Ala Ala Asn Pro Leu Gly Arg Pro Gly Glu Gly
            20                  25                  30

Val Cys Arg Ala Ile Tyr Lys Arg Trp Pro Thr Ser Phe Thr Asp Ser
        35                  40                  45

Ala Thr Glu Thr Gly Thr Ala Arg Met Thr Val Cys Leu Gly Lys Lys
    50                  55                  60

Val Ile His Ala Val Gly Pro Asp Phe Arg Lys His Pro Glu Ala Glu
65                  70                  75                  80

Ala Leu Lys Leu Leu Gln Asn Ala Tyr His Ala Val Ala Asp Leu Val
                85                  90                  95

Asn Glu His Asn Ile Lys Ser Val Ala Ile Pro Leu Leu Ser Thr Gly
            100                 105                 110

Ile Tyr Ala Ala Gly Lys Asp Arg Leu Glu Val Ser Leu Asn Cys Leu
        115                 120                 125

Thr Thr Ala Leu Asp Arg Thr Asp Ala Asp Val Thr Ile Tyr Cys Leu
    130                 135                 140

Asp Lys Lys Trp Lys Glu Arg Ile Asp Ala Ala Leu Gln Leu Lys Glu
145                 150                 155                 160

Ser Val Thr Glu Leu Lys Asp Glu Asp Met Glu Ile Asp Asp Glu Leu
                165                 170                 175

Val Trp Ile His Pro Asp Ser Cys Leu Lys Gly Arg Lys Gly Phe Ser
            180                 185                 190

Thr Thr Lys Gly Lys Leu Tyr Ser Tyr Phe Glu Gly Thr Lys Phe His
        195                 200                 205

Gln Ala Ala Lys Asp Met Ala Glu Ile Lys Val Leu Phe Pro Asn Asp
    210                 215                 220

Gln Glu Ser Asn Glu Gln Leu Cys Ala Tyr Ile Leu Gly Glu Thr Met
225                 230                 235                 240

Glu Ala Ile Arg Glu Lys Cys Pro Val Asp His Asn Pro Ser Ser Ser
                245                 250                 255

Pro Pro Lys Thr Leu Pro Cys Leu Cys Met Tyr Ala Met Thr Pro Glu
            260                 265                 270

Arg Val His Arg Leu Arg Ser Asn Asn Val Lys Glu Val Thr Val Cys
        275                 280                 285

Ser Ser Thr Pro Leu Pro Lys His Lys Ile Lys Asn Val Gln Lys Val
    290                 295                 300

Gln Cys Thr Lys Val Val Leu Phe Asn Pro His Thr Pro Ala Phe Val
305                 310                 315                 320

Pro Ala Arg Lys Tyr Ile Glu Val Pro Glu Gln Pro Thr Ala Pro Pro
                325                 330                 335

Ala Gln Ala Glu Glu Ala Pro Glu Val Val Ala Thr Pro Ser Pro Ser
            340                 345                 350

Thr Ala Asp Asn Thr Ser Leu Asp Val Thr Asp Ile Ser Leu Asp Met
        355                 360                 365

Asp Asp Ser Ser Glu Gly Ser Leu Phe Ser Ser Phe Ser Gly Ser Asp
    370                 375                 380

Asn Ser Ile Thr Ser Met Asp Ser Trp Ser Ser Gly Pro Ser Ser Leu
385                 390                 395                 400
```

```
Glu Ile Val Asp Arg Arg Gln Val Val Ala Asp Val His Ala Val
            405                 410                 415

Gln Glu Pro Ala Pro Ile Pro Pro Arg Leu Lys Lys Met Ala Arg
            420                 425                 430

Leu Ala Ala Ala Arg Lys Glu Pro Thr Pro Pro Ala Ser Asn Ser Ser
                435                 440                 445

Glu Ser Leu His Leu Ser Phe Gly Gly Val Ser Met Ser Leu Gly Ser
450                 455                 460

Ile Phe Asp Gly Glu Thr Ala Arg Gln Ala Ala Val Gln Pro Leu Ala
465                 470                 475                 480

Thr Gly Pro Thr Asp Val Pro Met Ser Phe Gly Ser Phe Ser Asp Gly
                485                 490                 495

Glu Ile Asp Glu Leu Ser Arg Arg Val Thr Glu Ser Glu Pro Val Leu
                500                 505                 510

Phe Gly Ser Phe Glu Pro Gly Glu Val Asn Ser Ile Ile Ser Ser Arg
                515                 520                 525

Ser Ala Val Ser Phe Pro Leu Arg Lys Gln Arg Arg Arg Arg Arg Ser
530                 535                 540

Arg Arg Thr Glu Tyr
545

<210> SEQ ID NO 8
<211> LENGTH: 616
<212> TYPE: PRT
<213> ORGANISM: Sindbis virus

<400> SEQUENCE: 8

Leu Thr Gly Val Gly Gly Tyr Ile Phe Ser Thr Asp Thr Gly Pro Gly
1               5                   10                  15

His Leu Gln Lys Lys Ser Val Leu Gln Asn Gln Leu Thr Glu Pro Thr
                20                  25                  30

Leu Glu Arg Asn Val Leu Glu Arg Ile His Ala Pro Val Leu Asp Thr
            35                  40                  45

Ser Lys Glu Glu Gln Leu Lys Leu Arg Tyr Gln Met Met Pro Thr Glu
50                  55                  60

Ala Asn Lys Ser Arg Tyr Gln Ser Arg Lys Val Glu Asn Gln Lys Ala
65                  70                  75                  80

Ile Thr Thr Glu Arg Leu Leu Ser Gly Leu Arg Leu Tyr Asn Ser Ala
                85                  90                  95

Thr Asp Gln Pro Glu Cys Tyr Lys Ile Thr Tyr Pro Lys Pro Leu Tyr
            100                 105                 110

Ser Ser Ser Val Pro Ala Asn Tyr Ser Asp Pro Gln Phe Ala Val Ala
        115                 120                 125

Val Cys Asn Asn Tyr Leu His Glu Asn Tyr Pro Thr Val Ala Ser Tyr
130                 135                 140

Gln Ile Thr Asp Glu Tyr Asp Ala Tyr Leu Asp Met Val Asp Gly Thr
145                 150                 155                 160

Val Ala Cys Leu Asp Thr Ala Thr Phe Cys Pro Ala Lys Leu Arg Ser
                165                 170                 175

Tyr Pro Lys Lys His Glu Tyr Arg Ala Pro Asn Ile Arg Ser Ala Val
            180                 185                 190

Pro Ser Ala Met Gln Asn Thr Leu Gln Asn Val Leu Ile Ala Ala Thr
        195                 200                 205

Lys Arg Asn Cys Asn Val Thr Gln Met Arg Glu Leu Pro Thr Leu Asp
```

```
            210                 215                 220
Ser Ala Thr Phe Asn Val Glu Cys Phe Arg Lys Tyr Ala Cys Asn Asp
225                 230                 235                 240

Glu Tyr Trp Glu Glu Phe Ala Arg Lys Pro Ile Arg Ile Thr Thr Glu
                245                 250                 255

Phe Val Thr Ala Tyr Val Ala Arg Leu Lys Gly Pro Lys Ala Ala Ala
                    260                 265                 270

Leu Phe Ala Lys Thr Tyr Asn Leu Val Pro Leu Gln Glu Val Pro Met
                275                 280                 285

Asp Arg Phe Val Met Asp Met Lys Arg Asp Val Lys Val Thr Pro Gly
            290                 295                 300

Thr Lys His Thr Glu Glu Arg Pro Lys Val Gln Val Ile Gln Ala Ala
305                 310                 315                 320

Glu Pro Leu Ala Thr Ala Tyr Leu Cys Gly Ile His Arg Glu Leu Val
                    325                 330                 335

Arg Arg Leu Thr Ala Val Leu Leu Pro Asn Ile His Thr Leu Phe Asp
                340                 345                 350

Met Ser Ala Glu Asp Phe Asp Ala Ile Ile Ala Glu His Phe Lys Gln
                355                 360                 365

Gly Asp Pro Val Leu Glu Thr Asp Ile Ala Ser Phe Asp Lys Ser Gln
                370                 375                 380

Asp Asp Ala Met Ala Leu Thr Gly Leu Met Ile Leu Glu Asp Leu Gly
385                 390                 395                 400

Val Asp Gln Pro Leu Leu Asp Leu Ile Glu Cys Ala Phe Gly Glu Ile
                    405                 410                 415

Ser Ser Thr His Leu Pro Thr Gly Thr Arg Phe Lys Phe Gly Ala Met
                420                 425                 430

Met Lys Ser Gly Met Phe Leu Thr Leu Phe Val Asn Thr Val Leu Asn
                435                 440                 445

Val Val Ile Ala Ser Arg Val Leu Glu Glu Arg Leu Lys Thr Ser Arg
450                 455                 460

Cys Ala Ala Phe Ile Gly Asp Asp Asn Ile Ile His Gly Val Val Ser
465                 470                 475                 480

Asp Lys Glu Met Ala Glu Arg Cys Ala Thr Trp Leu Asn Met Glu Val
                    485                 490                 495

Lys Ile Ile Asp Ala Val Ile Gly Glu Arg Pro Pro Tyr Phe Cys Gly
                500                 505                 510

Gly Phe Ile Leu Gln Asp Ser Val Thr Ser Thr Ala Cys Arg Val Ala
                515                 520                 525

Asp Pro Leu Lys Arg Leu Phe Lys Leu Gly Lys Pro Leu Pro Ala Asp
530                 535                 540

Asp Glu Gln Asp Glu Asp Arg Arg Arg Ala Leu Leu Asp Glu Thr Lys
545                 550                 555                 560

Ala Trp Phe Arg Val Gly Ile Thr Gly Thr Leu Ala Val Ala Val Thr
                    565                 570                 575

Thr Arg Tyr Glu Val Asp Asn Ile Thr Pro Val Leu Leu Ala Leu Arg
                580                 585                 590

Thr Phe Ala Gln Ser Lys Arg Ala Phe Gln Ala Ile Arg Gly Glu Ile
                595                 600                 605

Lys His Leu Tyr Gly Gly Pro Lys
610                 615
```

<210> SEQ ID NO 9

```
<211> LENGTH: 159
<212> TYPE: PRT
<213> ORGANISM: Artificial Sequence
<220> FEATURE:
<223> OTHER INFORMATION: Escherichia coli recombinant protein

<400> SEQUENCE: 9

Met Ile Ser Leu Ile Ala Ala Leu Ala Val Asp His Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155

<210> SEQ ID NO 10
<211> LENGTH: 245
<212> TYPE: PRT
<213> ORGANISM: Artificial Sequence
<220> FEATURE:
<223> OTHER INFORMATION: Homo sapiens recombinant protein

<400> SEQUENCE: 10

Ser Leu Ala Leu Ser Leu Thr Ala Asp Gln Met Val Ser Ala Leu Leu
1               5                   10                  15

Asp Ala Glu Pro Pro Ile Leu Tyr Ser Glu Tyr Asp Pro Thr Arg Pro
            20                  25                  30

Phe Ser Glu Ala Ser Met Met Gly Leu Leu Thr Asn Leu Ala Asp Arg
        35                  40                  45

Glu Leu Val His Met Ile Asn Trp Ala Lys Arg Val Pro Gly Phe Val
    50                  55                  60

Asp Leu Ala Leu His Asp Gln Val His Leu Leu Glu Cys Ala Trp Met
65                  70                  75                  80

Glu Ile Leu Met Ile Gly Leu Val Trp Arg Ser Met Glu His Pro Gly
                85                  90                  95

Lys Leu Leu Phe Ala Pro Asn Leu Leu Leu Asp Arg Asn Gln Gly Lys
            100                 105                 110

Cys Val Glu Gly Gly Val Glu Ile Phe Asp Met Leu Leu Ala Thr Ser
        115                 120                 125

Ser Arg Phe Arg Met Met Asn Leu Gln Gly Glu Glu Phe Val Cys Leu
    130                 135                 140

Lys Ser Ile Ile Leu Leu Asn Ser Gly Val Tyr Thr Phe Leu Ser Ser
145                 150                 155                 160

Thr Leu Lys Ser Leu Glu Glu Lys Asp His Ile His Arg Val Leu Asp
```

```
                    165                 170                 175
Lys Ile Thr Asp Thr Leu Ile His Leu Met Ala Lys Ala Gly Leu Thr
                180                 185                 190

Leu Gln Gln Gln His Gln Arg Leu Ala Gln Leu Leu Leu Ile Leu Ser
            195                 200                 205

His Ile Arg His Met Ser Ser Lys Arg Met Glu His Leu Tyr Ser Met
        210                 215                 220

Lys Cys Lys Asn Val Val Pro Leu Ser Asp Leu Leu Leu Glu Met Leu
225                 230                 235                 240

Asp Ala His Arg Leu
                245

<210> SEQ ID NO 11
<211> LENGTH: 108
<212> TYPE: PRT
<213> ORGANISM: Artificial Sequence
<220> FEATURE:
<223> OTHER INFORMATION: Homo sapiens recombinant protein

<400> SEQUENCE: 11

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Val Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105

<210> SEQ ID NO 12
<211> LENGTH: 4
<212> TYPE: PRT
<213> ORGANISM: Artificial Sequence
<220> FEATURE:
<223> OTHER INFORMATION: Synthetic

<400> SEQUENCE: 12

Gly Gly Gly Ser
1
```